United States Patent

Bernat et al.

[11] Patent Number: 6,057,318
[45] Date of Patent: May 2, 2000

[54] HETEROCYCLIC DERIVATIVES, PROCESS FOR THEIR PREPARATION AND THEIR THERAPEUTIC USE

[75] Inventors: André Bernat, Cugnaux; Jean-Marc Herbert, Plaisance du Touch; Gérard Valette, Lacroix, all of France

[73] Assignee: Sanofi, Paris, France

[21] Appl. No.: 09/081,782

[22] Filed: May 20, 1998

Related U.S. Application Data

[62] Division of application No. 08/511,468, Aug. 4, 1995, Pat. No. 5,780,468, which is a division of application No. 08/111,732, Aug. 25, 1993, Pat. No. 5,470,855, which is a continuation of application No. 07/743,309, filed as application No. PCT/FR90/00970, Dec. 28, 1990, abandoned.

[30] Foreign Application Priority Data

Dec. 29, 1998 [FR] France ................................. 89 17491

[51] Int. Cl.⁷ ..................... A61K 31/497; A61K 31/535; C07D 417/12
[52] U.S. Cl. ..................... 514/236.8; 514/321; 514/366; 514/255; 544/133; 544/368; 546/198; 548/150
[58] Field of Search ............................ 514/236.8, 255, 514/318, 342, 422, 366, 321; 546/209, 281.1, 198; 544/133, 368; 548/150

[56] References Cited

FOREIGN PATENT DOCUMENTS

| 0149884 | 8/1984 | European Pat. Off. ............... 546/280 |
| 0283390 | 9/1988 | European Pat. Off. ............... 544/133 |
| 880749 | 6/1953 | Germany ............................... 544/330 |

*Primary Examiner*—Alan L. Rotman

*Attorney, Agent, or Firm*—Jacobson, Price, Holman & Stern, PLLC

[57] ABSTRACT

The invention relates to compounds of formula:

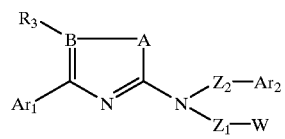

in which:

A is selected from O or S; B is selected from C or N;

$Z_1$ is selected from $C_1$–$C_4$ alkylene or phenylene;

$Z_2$ is $C_1$–$C_4$ alkylene; W is $NR_1R_2$, in which $R_1$ is selected from H or $C_1$–$C_4$ alkyl and $R_2$ is selected from H, $C_1$–$C_4$ alkyl, $CONQ_1Q_2$ or $CSNQ_1Q_2$ in which $Q_1$ and $Q_2$ are independently selected from H or $C_1$–$C_4$ alkyl, $SO_2Q_3$ or $COQ_3$ in which $Q_3$ is $C_1$–$C_4$ alkyl, $COOQ_4$ in which $Q_4$ is selected from $C_1$–$C_4$ alkyl or benzyl, or $R_1$ and $R_2$ taken together with N form a saturated heterocycle, or W is selected from $C_1$–$C_4$ alkoxy or thioalkoxy, $CONQ_1Q_2$ or $CSNQ_1Q_2$, pyridyl, imidazolyl or $COOQ_5$ in which $Q_5$ is $C_1$–$C_5$ alkyl; $R_3$ is not present when B is N, or is H, $C_1$–$C_8$ alkyl or halogen; $Ar_1$ is selected from optionally substituted phenyl, thienyl, furyl, indolyl, naphthyl or benzyl or $Ar_1$ and $R_3$ taken together form a phenylalkylene group; $Ar_2$ is selected from pyrimidinyl, quinolyl, isoquinolyl, indolyl, isoindolyl or pyridyl, optionally substituted; as well as their salts.

Use as medicines.

4 Claims, No Drawings

HETEROCYCLIC DERIVATIVES, PROCESS FOR THEIR PREPARATION AND THEIR THERAPEUTIC USE

CROSS-REFERENCE

This application is a division of Ser. No. 08/511,468 filed Aug. 4, 1995, U.S. Pat. No. 5,780,468, which is a division of Ser. No. 08/111,732 filed Aug. 25, 1993 U.S. Pat. No. 5,470,855, which is a continuation of Ser. No. 07/743,309 filed Aug. 26, 1991 abandoned, which is a 371 of PCT/FR90/00970 filed Dec. 28, 1990.

DETAILED DESCRIPTION

The present invention relates to heterocyclic derivatives, a process for their preparation and their therapeutic use.

In EP-A-0 283 390 2-amino thiazole derivatives of formula:

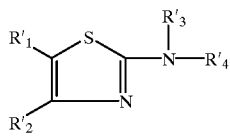

were described in which $R'_2$ denotes, among others an aromatic group, $R'_3$ is selected from H or $C_1-C_4$ alkyl and $R'_4$ is an aminoalkyl group in which the nitrogen of the amino group may, in particular, be included in a heterocycle such as pyridine, pyrrolidine, piperidine or piperazine; these compounds are agonists of the central muscarinic receptors and exhibit a stimulating activity on cholinergic transmission in the central nervous system.

2-amino 4,5-diphenyl oxazoles, disubstituted on the amino group by hydroxy alkyl or alkyl, and having an antithrombotic activity, were described in FR-1 538009, whereas those substituted on the amino group by alkyl and hydroxyalkyl, and having an anti-inflammatory activity, were described in DE-2 518 882.

Among the derivatives of 2-amino 4-phenyl 1,2,4-thiazoles, the antimalarial derivatives described in J. Het. Chem. 10, 611 (1973) may be mentioned in which the amine function is substituted by dialkylaminoalkyl and thiadizolyl, or the anethetics described in CH-497 453 which are substituted on the amine function by alkyl and aminoalkyl.

Among the 2-amino 4-phenyl 1,2,4-oxadiazole derivatives, the local anesthetics and vasodilatators described in FR-2 148 430, which are disubstituted on the amine function by dialkylaminoalkyl, may be mentioned.

The compounds according to the invention have none of these activities but are antagonists of the PAF-acether (platelet activating factor); they correspond to the formula:

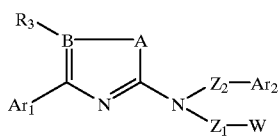

in which
A is selected from O or S;
B is selected from C or N;
$Z_1$ is selected from $C_1-C_4$ alkylene or phenylene;
$Z_2$ is $C_1-C_4$ alkylene;

W is $NR_1R_2$, in which $R_1$ is selected from H or $C_1-C_4$ alkyl and $R_2$ is selected from H, $C_1-C_4$ alkyl, $CONQ_1Q_2$ or $CSNQ_1Q_2$ in which $Q_1$ and $Q_2$ are independently selected from H or $C_1-C_4$ alkyl, $SO_2Q_3$ or $COQ_3$ in which $Q_3$ is $C_1-C_4$ alkyl, $COOQ_4$ in which $Q_4$ is selected from $C_1-C_4$ alkyl or benzyl, or $R_1$ and $R_2$ taken together with N form a saturated heterocycle such as morpholine, pyrrolidine, piperidine, piperazine or 4-($C_1-C_4$)alkyl-piperazine, or W may be the N-oxide of the amines $NR_1R_2$, or W may also be selected from $C_1-C_4$ alkoxy or thioalkoxy, $CONQ_1Q_2$ or $CSNQ_1Q_2$, pyridyl, imidazolyl or $COOQ_5$ in which $Q_5$ is $C_1-C_5$ alkyl; $R_2$ is not present when B is N, or is selected from H, $C_1-C_8$ alkyl or halogen when B is C; $Ar_1$ is phenyl optionally substituted by one or more groups selected from halogeno, $C_1-C_4$ alkyl, alkoxy or thioalkoxy, hydroxy, carboxy, $COOQ_6$ or $COSO_6$ or $CSOQ_6$ in which $Q_6$ is $C_1-C_4$ alkyl, carboxamido, cyano, amino, acetamido, nitro, trifluoromethyl, or $Ar_1$ is selected from an aromatic heterocycle, thienyl, furyl, indolyl or $Ar_1$ is also selected from naphthyl, benzyl or cyclohexyl, or $Ar_1$ and $R_3$ taken together form a group

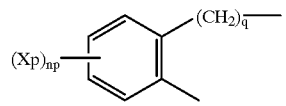

such that the carbon of the phenyl is linked to position 4 of the heterocycle and in which q equals 2 to 4, Xp, identical or different, are selected from H, $C_1-C_3$ alkyl or halogen and n is 1 to 3; $Ar_2$ is selected from an aromatic nitrogenous heterocycle, pyrimidinyl, quinolyl, isoquinolyl, indolyl, isoindolyl or pyridyl, optionally substituted by $C_1-C_3$ alkyl or alkoxy or halogen; as well as the salts of these compounds with acids or bases.

The alkyl, alkylene, alkoxy, thioalkoxy groups are linear or branched.

The salts with pharmaceutically acceptable acids or bases are preferred but those which may be used to isolate, and in particular purify, the compounds of formula I are also within the invention.

Compounds are preferred in which B is a carbon atom and particularly the derivatives of thiazole in which $Ar_1$ is a phenyl ring at least ortho substituted or those in which $Ar_1$ is phenyl without an ortho substituent and $R_3$ is selected from halogen or $C_1-C_3$ alkyl; W is preferably selected from $C_1-C_2$ alkoxy or thioalkoxy or also $NR_1R_2$ in which $R_1$, $R_2$ are independently selected from H or $C_1-C_4$ alkyl or $NR_1R_2$ form a saturated heterocycle; finally, $Z_1$ is preferably selected from ethylene or propylene.

Among the latter, a preferred group of compounds may be represented by the formula II:

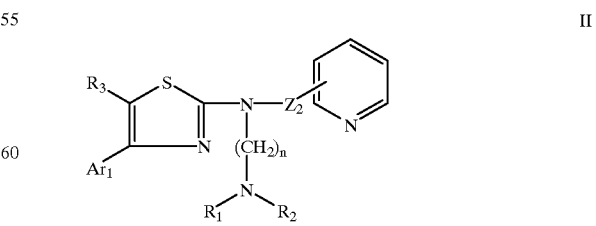

in which
$R_1$ and $R_2$ is each selected from hydrogen or $C_1-C_3$ alkyl, or form together with the nitrogen to which they are attached pyrrolidinyl or piperidino, $Z_2$ is selected from $CH_2$ or $CHCH_3$, $R_3$ is H and $Ar_1$ is a phenyl group bearing at least an ortho substituent or $R_3$ is selected from Cl, Br or $C_1$–$C_6$ alkyl and $Ar_1$ is phenyl, optionally substituted, the substituents of the phenyl groups being selected from halogen and $C_1$–$C_4$ alkyl or alkoxy, and n equals 2 or 3.

As will be seen hereafter, compounds of special interest correspond to the formula:

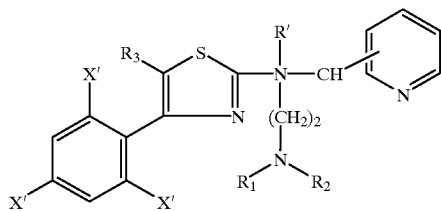

III in which
R_3 is selected from H or halogen such as Br or Cl, R' is selected from H or $CH_3$, X' is $C_1$–$C_4$ alkyl, and $R_1$ and $R_2$ is each separately selected from H or $C_1$–$C_3$ alkyl or together with the nitrogen from which they are attached pyrrolidinyl or piperidino, and the pyridyl group being substituted at position 2 or 3.

Among the preferred compounds, mention may be made for example of 2-(N-[2-(N',N'-dimethylamino)ethyl]N-[3-pyridylmethyl]amino) 4-(2,4,6-triisopropylphenyl)thiazole, 2-(N-[2-N',N'-dimethylaminoethyl]N-[3-pyridylmethyl] amino) 4-(2,4,6-trimethylphenyl)thiazole, the 2-(N-[2-N', N'-dimethylaminoethyl]N-[3-pyridylmethyl]amino 4-(2,4-dichlorophenyl) 5-methyl derivatives of thiazole and oxazole and 2-(N-2[-N',N'-dimethylaminoethyl]N-[3-pyridylmethyl]amino) 4-(2,4,6-triisopropylphenyl) 5-chloro (or bromo) thiazole.

The processes for preparation of the compounds of formula I are another subject matter of the invention.

According to a first aspect, the compunds are prepared by reaction of the secondary amine of formula IV with the heterocycle of formula V bearing a nucleofuge substituent X such as halogen or sulfonate according to the reaction scheme (a)

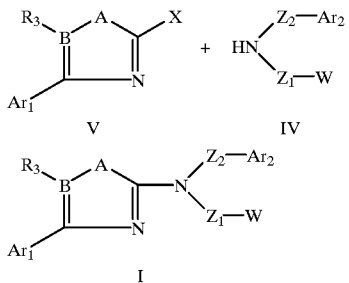

in which
A, B, $R_3$, $Ar_1$, $Z_2$, $Ar_2$, $Z_1$, W are as defined in formula I, with the exception that $R_3$=halogen, or $Ar_1$, $Ar_2$, W are equivalent groups in which the reactive functions have been protected in a standard manner. When A is selected from O or S and B is C, it is preferred that X be Br, and that the substitution is carried out in an aprotic solvent non-polar such as an aliphatic or aromatic hydrocarbon, preferably in the presence of a base in order to neutralize the acid formed; when A is selected from O or S and B is N, it is preferable that X be Cl, and that the substitution is carried out in an inert solvent such as an alcohol, an aliphatic or aromatic hydrocarbon, a ketone or a chlorinated solvent, such as methylene chloride.

The compounds of formula I may also be prepared from compunds of formula V in 2 steps, by first reacting a primary amine $Ar_2$-$Z_2$-$NH_2$ or W-$Z_1$-$NH_2$, then a halide or a sulfonate of formula W-$Z_1$-Y or $Ar_2$-$Z_2$-Y, respectively, with the secondary amine obtained preferably in the presence of a base. When A is O and B is N in the compound of formula V used in the first step X may be $CCl_3$.

In the case in which the compounds of formula I contain thiazole as heterocycle, it is also possible to prepare the appropriately substituted aminothiazole directly, either by reaction of an appropriately substituted thiourea with an alpha-halogenated ketone or by reaction of the secondary amine with an alpha-thiocyanatoketone according to the reactions schemes (b)

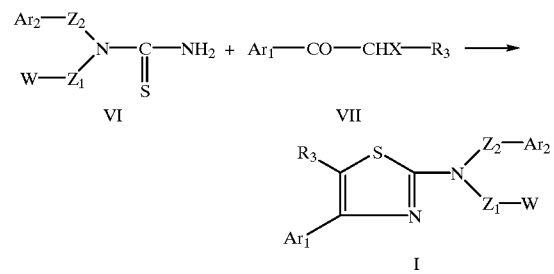

in which
W, $R_3$, $Z_1$, $Z_2$, $Ar_1$ and $Ar_2$ are as defined in formula I, with the exception of halogeno for $R_3$, or W, $Ar_1$, $Ar_2$ represent equivalent groups in which the reactive functions have been protected in a standard manner and X is halogen, in particular chlorine or bromine, and preferably bromine, and (c)

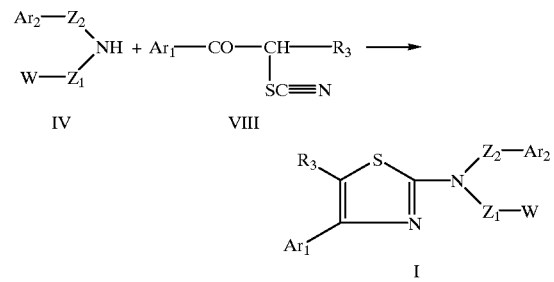

in which
W, $R_3$, $Z_1$, $Z_2$, $Ar_1$ and $Ar_2$ are as defined in formula I, with the exception of halogeno for $R_3$, or that W, $Ar_1$, $Ar_2$ represent equivalent groups in which the reactive functions have been protected in a standard manner.

In the case (b), the compound VII may optionally be used after the carbonyl function has been protected in the form of an acetal group, which will be eliminated during the cyclizing condensation; the reaction conditions are those usually used for this type of reaction, and reference may be made to the review by G. Vernin, Heterocyclic compounds 34/1/ 165–269 (1979) J. V. Metzger Ed. J. Wiley and Sons.

More particularly, the reaction is carried out in a polar solvent at a temperature between 40° C. and 100° C. Among the solvents which are suitable, mention may be made of alcohols, such as ethanol, methanol or isopropanol, aliphatic acids, such as acetic acid, nitriles such as acetonitrile, ethers such as dioxane or tetrahydrofuran. It is preferable to add a strong acid to the reaction mixture to accelerate the reaction when the thioureas of formula VI are not degraded in acidic medium.

In the case (c), as a general rule, a solution of the compounds IV and VIII in an inert solvent such as an aliphatic or aromatic hydrocarbon is stirred for several hours at a temperature between room temperature, i.e. about 20° C., and the reflux temperature of the selected solvent, and preferably at a temperature between 60° C. and 110° C.

When the compounds of formulae IV and VIII used bear functions which might react under the experimental conditions used for the preparation of the compounds of formula I, these latter are protected beforehand; thus when W is $NR_1R_2$ and $R_1$ and/or $R_2$ are H, the amine function may be blocked in the form of a carbamate, in particular by coupling the tert.butoxycarbonyl group to the nitrogen from which its removal is known to be easily carried out by reaction with an anhydrous acid such as trifluoroacetic acid or hydrochloric acid; when $Ar_1$, $Ar_1$ or W bear an acidic function, the compound of formula I bearing the corresponding $C_1$–$C_4$ alkyl ester function, which is customarily hydrolyzed in basic or possibly acidic medium, is prepared beforehand; when $Ar_1$ or $Ar_2$ bear a primary amine function, the compound of formula I bearing an acetamide function, which is hydrolysed in acidic or basic medium, is prepared beforehand.

Furthermore, in the cases in which W is $NR_1R_2$ with $R_2$ being selected from $CONQ_1Q_2$, $CSNQ_1Q_2$, $SO_2Q_3$, $COQ_3$, the compounds of formula I may be prepared from those in which $R_2$ is H.

The compounds of formula I in which $R_3$ is halogen are prepared by reaction of the halogen, $Cl_2$, $Br_2$ or ICl with the corresponding compound of formula I in which $R_3$ is H by applying in particular the method described for the thiazoles in J. Am. Chem. Soc. 68 453–458 (1946).

The products of formula I are isolated from the reaction medium and purified by the standard techniques by taking into account their physico-chemical properties and, in particular, their basic character. Some of these products are oily, and it is thus preferable to isolate them in the form of an addition salt with a mineral or organic acid, a salt which is sometimes hydrated or solvated; the salts are prepared by the reaction of an acid with the compound of formula I in solution, for example, in an alcohol or an ether and are isolated either by precipitation or by evaporation of the solvent; all or only some of the amine functions of the molecule may be converted into a salt depending on the experimental conditions and the acid used.

The N-oxide of the amine function may be prepared by reaction of a suitable oxidizing agent with a compound of formula I, in particular reaction with 2-phenylsulfonyl 3-phenyl oxaziridine according to the procedure described in J. Org. Chem. 53 p. 5856 (1988).

Under these conditions the nitrogen atoms of the heterocycle and $Ar_2$ are not oxidized.

Most of the products of formulae IV to VIII are not commercially available and some are new, but they bay be prepared by processes, the principle of which is know and the implementation of which has been described for similar products.

Thus the secondary amines of formula IV are prepared from the primary amines $Ar_2$—$Z_2$—$NH_2$ or W—$Z_1$—$NH_2$, in which the reactive functions are optionally protected:

either by means of a nucleophilic substitution reaction in which a compound of either formula $Ar_2$—$Z_2$—Y or formula W—$Z_1$—Y, in which Y is selected from halogen or a sulfonate group $ZSO_3$— in which Z is selected from $C_1$-$C_4$ alkyl or optionally substituted phenyl, is reacted with the primary amine.

or by the condensation of the primary amine with a ketone or an aldehyde in a dehydrating medium, followed by the reduction of the imine formed in a standard manner by means of a metal hydride or by hydrogen in the presence of a catalyst, such as Pd, in accordance with the following reaction scheme (d):

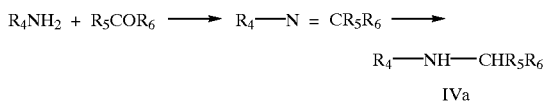

in which $R_4$ is —$Z_2Ar_2$, in the case in which —$CHR_5R_6$ is —$Z_1W$ or $R_4$ is —$Z_1W$ in the case in which —$CHR_5R_6$ is —$Z_2Ar_2$, according to a process described in particular in Methoden Org. Chemie IV/1d/355–363, (1981).

The ketones of formula VII may be prepared by halogenation of the ketones of formula $Ar_1COCH_2R_3$, which are usually know and often commercially available; when not, they may be prepared, in particular, by the Friedel Crafts reaction between $Ar_1H$ and $R_3CH_2COCl$ in the presence of a Lewis acid.

The alpha-brominated ketones are prepared from $Ar_1COCH_2R_3$, in particular by reaction with bromine in a solvent such as acetic acid, carbon tetrachloride or an ether such as ethyl ether, by reaction with cupric bromide by employing the method described in J. Org. Chem. 29 p. 3459–3461 (1964), reaction with quaternary ammonium tribromides as described in Bull. Chem. Soc. Japan 60 1159–1160 and 2667–2668 (1987); alpha-chlorinated ketones may be prepared by reaction with quaternary ammonium dichloroiodates, as described in Synthesis p. 545–546 (1988).

In some cases, it is advantageous to prepare the alpha-brominated ketones by a Friedel Crafts reaction between the aromatic derivative of formula $Ar_1H$ and the acid chloride $R_3$—CHBr—COCl, by employing the method described in Methoden der Org. Chemie VII/2a/p. 110–132 (1977).

Finally, when $R_3$ is H, it is possible to start from the acid chloride $Ar_1COCl$ which is reacted with diazomethane, a reaction followed by hydrolysis of the diazoketone obtained by means of a halogen acid, a method described in particular in Org. Synth. Coll. vol. 3 p. 119–120, The thioureas of formula VI may be prepared through the intermediary of the compound of formula IX

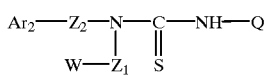

resulting from the reaction between a secondary amine of formula IV and an isothiocyanate of formula Q—N=C=S, in which Q is an acyl group removable in an acidic medium, in particular acetyl, benzoyl or pivaloyl, and preferably pivaloyl; the derivative Q—N=C=S is itself prepared by reaction of the carboxylic acid chloride with a metal thiocyanate in an anhydrous solvent such as acetone or methylethyl ketone.

The compound of formula VI is obtained by the reaction of a strong acid on the compounds of formula IX, for example by reaction of an aqueous solution of HCl, in particular 12N HCl, at a temperature between 10° C. and 100° C.

The thiocyanatoketones of formula VIII may be prepared by reaction of a metal thiocyanate with the corresponding alpha-halogenated ketone of formula VII in an anhydrous solvent by employing the process of Tcherniac, described in particular in Heterocyclic compounds 34 (1) p. 271–273 (1979).

The 2-halogeno thiazoles of formula V in which A is S and B is C can be prepared by reaction of a halogen acid in anhydrous medium with a solution of the thiocyanatoketone of formula VIII according to the process described in Heterocyclic Compounds 34(1) p. 273–276 (1979).

The 2-halogeno oxazoles of formula V, in which A is O and B is C, may be prepared from the oxazolin-2-ones, in particular by reaction with phosphoryl chloride in the presence of a tertiary amine, according to the reaction scheme (e)

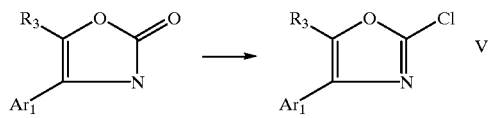

as described in Chem. Ber. 92 1928 (1959).

In the case of the processes for the preparation of the oxazolinones, reference may be made to the review by Y. S. Rao and R. Filler in Heterocyclic Compounds 45 p. 660–665 (1986), I. J. Turchi, Ed. J. Wiley and Sons. In particular, they may be prepared by cyclo-dehydration of the carbamates of formula X according to the reaction scheme (f)

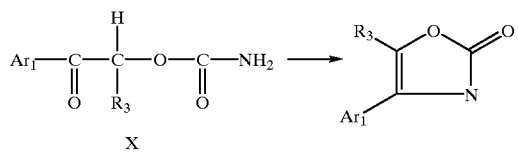

the carbamates themselves being obtained from the alpha-hydroxylated ketones $Ar_1$—O—CHOH—$R_3$.

The 5-chloro 1,2,4-thiadiazoles may be prepared by reaction of perchloromethylmercaptan with the amidine $Ar_1C(NH)NH_2$, according to a known process described in particular in Chem. Ber. 90 182–187 (1957).

The 5-chloro 1,2,4-oxadiazoles may be prepared by reaction of a chlorinating agent with the 1,2,4-oxadiazolin-5-ones, in particular by reaction with phosphorus oxychloride in the presence of an amine, as described in Yakugaku Zasshi 84 1061–1064 (1964) (Chem. Abs. 62 5270d).

Finally, the 5-trichloromethyl 1,2,4-oxadiazoles may be prepared by reaction of trichloroacetic anhydride with the amidoxime $Ar_1C(NOH)NH_2$, as described in Helv. Chem. Acta 46 1067–1073 (1963).

Examples of the preparation of intermediate compounds and compounds of formula I as well as their physico-chemical properties are given hereafter.

The specialist will be able to select the most suitable process for the preparation of a given compound of formula I by taking into consideration the available starting materials, the reactivity of the intermediates and their stability.

The compounds of formula I and their salts are antagonists of the PAF-acether. This phospholipid is a biological mediator whose chemical structure was determine in 1979 as being that of 1-0-hexadecyl 2-0-acetyl-sn-glycero-3-phosphorycholine, but whose release by the basophiles during anaphylactic reactions had been demonstrated as early as 1972. This mediator has many physiological activities including, for example, a potentiating effect on platelet aggregation, a constrictor effect on smooth muscle and the bronchi and a pro-inflammatory effect as well as a hypotensive activity.

Reference may be made to the article published in ISI Atlas of science: Pharmacology 1(3) p. 187–198 (1987) which reviews the physiological activities of PAF and the therapeutic uses of antagonists of this phospholipid implicated in many diseases, at least as an aggravating factor.

Different methods are known for demonstrating an antagonistic activity of the PAF.

Thus in vitro it is possible to study the inhibition of the aggregation of rabbit platelets induced by the PAF-acether according to the method described in Thrombosis Research 41 211–226 (1986). In this assay, most of the compounds of formula I, or their salts, have $IC_{50}$ (concentration inhibiting 50% of the aggregation induced by the PAF introduced into the medium at a concentration of $4 \times 10^{-10}$M, than $10^{-6}$M and in the case of many products of the order of $10^{-9}$M, whereas under the same conditions the compound know as WEB 2086, a known antagonist described in J. Pharmacol. Exper. Therap. 241, 974–981 (1987) has a $IC_{50}$ of $5 \times 10^{-8}$M. Among the most active compounds whose $IC_{50}$ is of the order of $10^{-9}$M and which exhibit a duration of action longer than WEB 2086, may be mentioned those of formula II already indicated.

Under the same experimental conditions, the compounds of formula I are inactive at a concentration $10^{-4}$M on the aggregation induced by arachidonic acid at a concentration of $10^{-4}$M or by adenosine $-5'$ diphosphate at a concentration of $10^{-5}$M.

Different methods have also been used to demonstrate in animals the inhibition of the effects of the PAF by antagonists, including that of the bronchospasm induced in the guinea pig, which is described in Thromb. Haemostas, 56,(1) 40–44 (1986) and that of protection against lethal systemic shock in the mouse, which is described in J. Pharmacol. Exp. Ther. 247(2) 617–23 (1988).

As an example, it is possible to show that the compounds of formula III indicated above completely inhibit the bronchospasm resulting from the intravenous (IV) injection of 100 ng/kg of PAF, when they are administered 1 hour before the injection either IV at a dose of 1 mg/kg or orally at a dose of 3 mg/kg; these same compounds reduce the mortality of the mice by 50% if they are administered 1 hour before the IV injection of 100 μg/kg of PAF at doses of the order of 0.5 mg/kg by the IV route and 10 mg/kg by the oral route. Among these latter, 2-(N-[2-N',N'-dimethylaminoethyl]N-[3-pyridylmethyl]amino) 4-(2,4,6-triisopropylphenyl) thiazole completely inhibits the bronchospasm induced in the guinea pig at an IV dose of 1 mg/kg or an oral dose of 3 mg/kg for more than 96 hours.

Furthermore, at an oral dose of 5 mg/kg, the compounds
2-(N-[2-N',N'-dimethylaminoethyl]N-[3-pyridylmethyl] amino)4-(2,4,6-trimethylphenyl)thiazole
2-(N-[2-N',N'-dimethylaminoethyl]N-[3-pyridylmethyl] amino)4-(2,4,6triisopropylphenyl) 5-chloro (or 5-bromo) thiazole.
2-(N-[2-N',N'-dimethylaminoethyl]N-[3-pyridylmethyl] amino)4-(2,4-dichlorophenyl) 5-methyl thiazole (or oxazole)

protect the mouse from the lethal systemic shock induced by the PAF at a dose of 100 μg/kg.

Thus, according to another aspect, the invention relates to the pharmaceutical compositions containing—as active ingredient—at least one compound of formula I or one of its pharmaceutically acceptable salts, in combination with the usual excipients for administration by the oral, rectal, transmucosal or parenteral routes. The unit and daily doses will depend on the compound, the nature and gravity of the disease, the patient and the route of administration; usually the unit dose by the oral route will be 5 mg to 500 mg in the adult, whereas by the intravenous route it will be 0.05 mg to 10 mg, these doses being compatible with the doses at which the pharmacological activity of these compounds is expressed in the animal without apparent toxic effect.

The compositions of the invention will be used in particular for the treatment of asthma, certain allergic or inflammatory conditions, cardiovascular diseases including atherosclerosis, thrombosis, hypotension or arrhythmias, cerebral and cardiac ischemias, and various renal diseases including glomerulonephrites, or even as a contraceptive agent.

First of all, in what follows the preparation of intermediate compounds of formula IV to VIII is described. The melting points mentioned are instant melting points; the boiling points were usually measured during distillation under reduced pressure.

Amines of formula IV

A) N,N-diisopropyl N'-(3-pyridylmethyl)ethanediamine. ($R_1=R_2=CH(CH_3)_2$; $Z_1=(CH_2)_2$; $Z_2=CH_2$; $Ar_2$=3-pyridyl)

Under an inert atmosphere, 16.9 g of 3-pyridyl carboxaldehyde are added to a solution of 25 g of N,N-diisopropyl ethanediamine in 150 ml of toluene in the presence of 4 Å molecular sieves.

After 1 hour at room temperature, the sieves are filtered off and the solvent is evaporated under reduced pressure at about 30° C.; the residual oil is taken up in 150 ml of anhydrous methanol and the solution is cooled to between 0 and 10° C. 6 g of sodium borohydride are then added in portions and the mixture is allowed to attain room temperature; after the mixture has been stirred for several hours 10 ml of an aqueous solution of 1N HCl are added, then an aqueous solution of 10N NaOH is added to give pH 8 before the final product is extracted with methylene chloride. The organic phase is dried over sodium sulfate, filtered and concentrated under reduced pressure at about 70° C. The oil obtained is distilled under vacuum. 30.1 g of the expected compound are obtained. B.p.:115° C./5 Pa.

B) N,N-dimethyl N'-(3-pyridylmethyl) ethanediamine. ($R_1=R_2=CH_3$; $Z_1=CH_2)_2$; $Z_2=CH_2$; $Ar_2$=3-pyridyl)

Under an inert atmosphere, 4 g of N,N-dimethylethanediamine are added to a cooled solution of 4.7 g of 3-pyridine carboxaldehyde in 40 ml of absolute ethanol in the presence of 4 Å molecular sieves.

After 1 hour at room temperature, the sieves are filtered off and 1.82 g of sodium borohydride are added to the solution cooled to between 0° C. and 10° C. After being stirred for 12 hours at room temperature, the mixture is concentrated under reduced pressure and 10 ml of an aqueous solution of N HCl are added to the residue; a concentrated solution of KOH is then added to give a pH higher than 8 and the mixture is extracted by ethyl ether; the organic phase is dried and the solvent removed under reduced pressure. The oil obtained is distilled under vacuum. 5.4 g of the expected compound are obtained. B.p.=84° C./40 Pa.

C) N,N-dimethyl N'-/1-(3-pyridyl)ethyl/ethanediamine ($R_1=R_2=CH_3$; $Z_1=(CH_2)$; $Z_2=CHCH_3$; $Ar_2$=3-pyridyl)

30 g of 3-acetyl pyridine, 28.4 g of N,N-dimethylethanediamine and 20 mg of para-toluene sulfonic acid are heated at reflux in 300 ml of anhydrous benzene for about 5 hours in a flask surmounted by a Dean-Stark tube.

After concentration under reduced pressure at about 50° C., the residual oil is taken up in 300 ml of anhydrous methanol and at a temperature lower than 10° C., 10 g of sodium borohydride are added and the reaction mixture is worked up under the conditions described in A. After distillation, 38 g of the expected compound are obtained. B.P.=96° C./60 Pa.

D) N-(piperidino ethyl) N-[1-(3-pyridyl)ethyl]amine

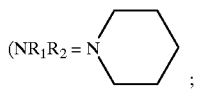

[$Z_1=[(CH_2)_2$; $Z_2=CH—CH_3$; $Ar_2$=3-pyridyl)

7.26 g of 3-acetyl pyridine, 8 g of piperidino-ethylamine, 0.2 g of para-toluene sulfonic acid are heated at reflux in 100 ml of toluene for about 3 hours in a flask surmounted by a Dean-Stark tube. The solvent is evaporated under vacuum at about 60° C. and the oil is taken up in 100 ml of anhydrous methanol. 2.3 g of sodium borohydride is then added in portions at about 5° C. After the mixture has been stirred overnight at room temperature, 10 ml of acetone are added to destroy the excess borohydride and after 15 minutes 15 ml of an aqueous solution of 5N NaOH are added. After concentration in a vacuum, the residue is extracted 3 times with 50 ml of methylene chloride. The organic phases are dried over anhydrous magnesium sulfate, filtered and concentrated under vacuum. After distillation, 11.5 g of the expected compound are obtained. B.p.=115° C./42 Pa.

E) N,N-[di-1-(3-pyridyl)ethyl]amine

W=3-pyridyl; $Z_1=Z_2=CHCH_3$: $Ar_2$=3-pyridyl

At about 5° C., 8.8 g of sodium cyanoborohydride are added in portions to a solution of 24.3 g of 3-acetyl pyridine and 157 g of ammonium acetate in 600 ml of methanol and the temperature is allowed to rise to about 20° C. After the mixture has been stirred for about 14 hours at room temperature, 50 g of 3-acetyl pyridine are added, then after stirring has been continued for several hours, the mixture is cooled to 5° C., 5 g of sodium cyanoborohydride are added. The temperature is then allowed to rise to room temperature and after being stirred for about 14 hours the mixture is concentrated to dryness at about 50° C. The residue is then acidified in a hood to give a pH close to 2 by the addition of an aqueous solution of 12N HCl, filtered and the filtrate is brought to about pH 8 by the addition of an aqueous solution of 10N NaOH. The aqueous phase is extracted by ethyl acetate and after drying of the organic phase and removal of the solvent, the residual oil is distilled in a vacuum at about 140° C. at a pressure of 21 Pa. 32 g of amine are thus obtained. The hydrochloride prepared by reaction of HCl with the amine dissolved in 400 ml of isopropanol melts above 250° C. The 2 diastereoisomers can be separated by fractional precipitation from aqueous methanol.

F) N,N-dimethyl N'-[2-(3-pyridyl)ethyl]ethanediamine ($R_1=R_2=CH_3$; $Z_1=(CH_2)_2$; $Z_2=(CH_2)_2$; $Ar_2$=3-pyridyl)

11 g of 3-(2-chloroethyl)pyridine hydrochloride, 16.3 g of N,N-dimethylethane diamine, 18.5 g of sodium bicarbonate and 13 g of potassium iodide are heated in 150 ml of ethanol for about 30 hours at about 60° C. The solvent is evaporated and the residue is taken up in 100 ml of water before an aqueous solution of 10N NaOH is added to give pH 8; the aqueous phase is then extracted 3 times with 80 ml of ethyl acetate. The pooled organic phases are dried over magnesium sulfate, filtered and concentrated under reduced pressure. The residual oil is distilled to give 6.7 g of the expected product. B.p.=100–107° C./10 Pa.

G) N-(tert.butyoxycarbonyl) N-methyl N'-(3-pyridylmethyl) ethanediamine ($R_1$=$CH_3$; $R_2$=t—$C_4H_9OCO$; $Z_1$=$(CH_2)_2$; $Z_2$=$CH_2$; $Ar_2$=3-pyridyl)

5.9 g of ditert.butyl dicarbonate in 60 ml of dioxane are added very slowly at about 3° C. to a mixture of 6 g of N-methyl N'-(3-pyridylmethyl)ethanediamine, 95 ml of dioxane, 20 ml of water and 1.74 g of magnesium oxide with stirring. After 15 minutes, 15 ml of approximately 2N sodium hydroxide are added to the mixture; the precipitate is then separated and the filtrate is concentrated under reduced pressure; the residue is dissolved in about 200 ml of ethyl acetate, then dried over sodium carbonate and the solvent is removed under reduced pressure after filtration of the solids. The residual oil is purified by chromatography on silica by eluting with ethyl ether followed by a methylene chloride/methanol mixture (95/5 v/v). The N,N' dicarbamate is eluted first, then the desired product (weight 3.9 g) before the carbamate formed at the nitrogen bearing the methylpyridyl group.

H) N-(3-pyridylmethyl) N'-(tert.butoxycarbonyl) ethanediamine ($R_1$=H; $R_2$=t—$C_4H_9OCO$; $Z_1$=$(CH_2)_2$; $Z_2$=$CH_2$; $AR_2$=3-pyridyl)

2.92 g of 3-pyridyl carboxaldehyde are added to a solution of 4.82 g of N-(tert.butoxycarbonyl)ethanediamine in 50 ml of toluene in the presence of a dehydrating agent (4 Å molecular sieves) at about 5° C.

The diamine may be prepared according to the method described in J. Med. Chem. 31 898 (1988). After 4 hours at room temperature, the sieves are separated and the solvent is evaporated under reduced pressure. The residual oil is dissolved in 30 ml of anhydrous methanol, and 0.68 g of sodium borohydride are added to the solution at 0° C. to 5° C. After the mixture has been stirred for 2 hours at room temperature, 10 ml of acetone are added, then the solvents are evaporated under reduced pressure. The residue is dissolved in 50 ml of methylene chloride saturated with water together with 0.5 g of KOH; the organic phase is then dried, the solvent is removed under reduced pressure and the residue is chromatographed on silica; the elution is carried out with a mixture of methylene chloride and methanol (90/10 v/v).

In this way, 5.1 g of amine are isolated in the form of an oil.

The amines in Table I were prepared by applying one of the above procedures.

TABLE 1

Amines IVa: $R_4NHCHR_5R_6$

| $R_4$ | $R_5$ | $R_6$ | Boiling point ° C./Pressure Pa |
|---|---|---|---|
| N,N-dimethylamino-2 ethyl | pyridyl-2 | H | 99–101/70 |
| N,N-dimethylamino-2 ethyl | pyridyl-4 | H | 110/70 |
| N,N-dimethylamino-2 ethyl | pyridyl-4 | $CH_3$ | 80/40 |
| N,N-dimethylamino-4 butyl | pyridyl-3 | H | 137/50 |
| N,N-dimethylamino-1 propyl-2 | pyridyl-3 | H | 113/40 |
| N,N-dimethylamino-3 propyl | pyridyl-3 | H | 103–108/10 |
| N,N-dimethylamino-3 propyl | pyridyl-3 | $CH_3$ | 107–110/20 |
| morpholino-3 propyl | pyridyl-3 | H | 140/2 |
| (imidazolyl-1)-3 propyl | pyridyl-3 | H | 175/5 |
| (imidazolyl-1)-3 propyl | pyridyl-3 | $CH_3$ | 169/10 |
| N,N-diethylamino-2 ethyl | pyridyl-3 | H | 104/10 |
| N,N-diethylamino-2 ethyl | pyridyl-3 | $CH_3$ | 103/6 |
| N,N-diisopropylamino-2 ethyl | pyridyl-3 | $CH_3$ | 116/7 |
| N,N-dibutylamino-2 ethyl | pyridyl-3 | $CH_3$ | 143/2 |
| (pyrrolidinyl-1)-2 ethyl | pyridyl-3 | H | 115–117/80 |
| (pyrrolidinyl-1)-2 ethyl | pyridyl-3 | $CH_3$ | 127/70 |

TABLE 1-continued

Amines IVa: $R_4NHCHR_5R_6$

| $R_4$ | $R_5$ | $R_6$ | Boiling point ° C./Pressure Pa |
|---|---|---|---|
| morpholino-2 ethyl | pyridyl-3 | H | 123/5 |
| morpholino-2 ethyl | pyridyl-3 | $CH_3$ | 130/4 |
| piperidino-2 ethyl | pyridyl-3 | H | 114/52 |
| methyl-4 piperazinyl-2 ethyl | pyridyl-3 | H | 170–175/3 |
| N-methyl N-phenyl amino-2 ethyl | pyridyl-3 | H | 135/4 |
| (ethyl-1 )pyrrolidinyl-2 ethyl | pyridyl-3 | $CH_3$ | 115/70 |
| pyridyl-2 methyl | pyridyl-3 | H | 135/4 |
| pyridyl-3 methyl | pyridyl-3 | H | 142/5 |
| N,N-dimethylamino-4 phenyl | pyridyl-3 | H | 160–166/40 |
| N,N-dimethylamino-2 ethyl | quinolyl-3 | H | 165–170/40 |
| N,N-dimethylamino-2 ethyl | (N-methyl)-indolyl-3 | H | 140/5 |
| N,N-dimethylamino-2 ethyl | (chloro-2) pyridyl-3 | H | 126/120 |
| methoxy-2 ethyl | pyridyl-3 | H | 78/94 |
| ethylthio-2 ethyl | pyridyl-3 | H | 70/13 |
| N,N-dimethylcarbamoylmethyl | pyridyl-3 | H | 142/4 |

Thioureas of Formula VI

I) N-(2-N',N'-dimethylaminoethyl) N-(3-pyridylmethyl) thiourea ($R_1$=$R_2$=$CH_3$; $Z_1$=$(CH_2)_2$; $Z_2$=$CH_2$; $Ar_2$=3-pyridyl)

i)—pivaloyl isothiocyanate: 18.7 g of pivaloyl chloride are added slowly to a suspension of 15.1 g of potassium thiocyanate in 150 ml of anhydrous acetone, cooled to about 4° C. The mixture is stirred for about 3 hours at this same temperature.

ii)—20 g of N-(2-dimethylaminoethyl) N-(3-pyridylmethyl) amine are added slowly to the above mixture while the temperature is maintained lower than 10° C. After one hour at room temperature, the mixture is evaporated to dryness under reduced pressure at about 60° C. and the residue is taken up in methylene chloride before being washed with a dilute solution of ammonia; the solvent is evaporated under reduced pressure and the oil obtained is taken up in about 100 ml of concentrated hydrochloric acid which is heated at about 80° C. for 1 hour. After being cooled, the solution is brought to pH 8 by the addition of an ice-cold solution of ammonia, then it is extracted 3 times with methylene chloride; the organic phases are dried over magnesium sulfate, the solids are removed and the filtrate is concentrated under reduced pressure at about 60° C. The oil obtained (41 g) may be used as such in the next step or purified by medium pressure chromatography on silica (eluent: methylene chloride/methanol 8/2 v/v). The pure product crystallizes from ethyl acetate, M.p.=104° C.

The thiourea synthetic intermediates of the examples were prepared by applying this method; the melting points of some of them are shown in Table 2.

TABLE 2

Thioureas :

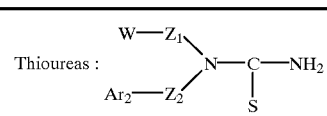

| $WZ_1$ | $Ar_2$—$Z_2$ | M.p. ° C. |
|---|---|---|
| pyridyl-2 methyl | pyridyl-3 methyl | 143 |
| pyridyl-3 methyl | pyridyl-3 methyl | 140 |
| N,N-dimethylamino-2 ethyl | (pyridyl-3)-2 ethyl | 89 |

TABLE 2-continued

Thioureas:

$$\begin{array}{c} W-Z_1 \\ Ar_2-Z_2 \end{array} N-\underset{\underset{S}{\|}}{C}-NH_2$$

| $WZ_1$ | $Ar_2-Z_2$ | M.p. °C. |
|---|---|---|
| N,N-diethylamino-2 ethyl | pyridyl-3 methyl | 78 |
| N,N-diisopropylamino-2 ethyl | pyridyl-3 methyl | 86 |
| N,N-diisopropylamino-2 ethyl | (pyridyl-3)-1 ethyl | 122 |
| (piperidinyl-1)-2 ethyl | pyridyl-3 methyl | 107 |
| morpholino-2 ethyl | pyridyl-3 methyl | 136–137 |
| morpholino-2 ethyl | (pyridyl-3)-1 ethyl | 145–146 |
| N,N-dimethylamino-3 propyl | pyridyl-3 methyl | 70 |
| N,N-dimethylamino-3 propyl | (pyridyl-3)-1 ethyl | 90 |
| morpholino-3 propyl | pyridyl-3 methyl | 146 |
| (imidazolyl-1)-3 propyl | pyridyl-3 methyl | 136–138 |
| N,N-dimethylamino-4 phenyl | pyridyl-3 methyl | 180 |
| N,N-dimethylamino-4 butyl | pyridyl-3 methyl | 82 |
| N,N-dimethylamino-2 ethyl | (chloro-2)pyridyl-3 methyl | 162 |

Alpha-bromoketones of Formula VII

J) 1-(2,4,6-trimethyl)phenyl 2-bromo ethanone
(VII: $Ar_1$=2,4,6-$(CH_3)_3$—$C_6H_2$; $R_3$=H; X=Br)

52 g of bromine are introduced slowly into a solution of 50 g of 1-(2,4,6-trimethylphenyl) ethanone in 100 ml of acetic acid at 10° C. After being stirred for 1 hour at this temperature and for 2 hours at about 20° C., the reaction mixture is poured into one volume of ice-cold water and extracted with ethyl ether. The organic phase is separated, washed with an aqueous 5% solution of $NaHCO_3$, then with water and, after drying over $MgSO_4$, is concentrated under reduced pressure at about 60° C. 66 g of oil are obtained which may be purified by distillation or crystallization from pentane at about −20° C. M.p.<50° C.

K) 1-(2-trifluoromethyl)phenyl 2-bromo ethanone
(VII: $Ar_1$=2-$(CF_3)$—$C_6H_4$; $R_3$=H; X=Br)

Under an inert atmosphere, 28.2 g of finely ground cupric bromide are introduced into a solution of 8.5 g of 1-(2-trifluoro methyl)phenyl ethanone in 25 ml of ethyl acetate and 25 ml of chloroform at reflux. The reaction mixture is maintained at its reflux temperature for 3 hours, then distilled under reduced pressure. In this way, 10.7 g of the ketone are obtained. B.p.=80° C./3 Pa.

L) 1-(2,4,6-triisopropyl)phenyl 2-bromo ethanone
(VII: $Ar_1$=2,4,6-/$(CH_3)_2CH$/—$C_6H_2$; $R_3$=H; X=Br)

Under an inert atmosphere, a solution of 25 g of 1,3,5-triisopropyl benzene in 50 ml of 1,2-dichloroethane are introduced into a suspension of 16.5 g of anhydrous aluminium chloride in 200 ml of 1,2-dichloromethane at 0° C.

After the reaction mixture has been stirred for 30 minutes at this temperature, 20.7 g of bromoacetyl chloride are added slowly, then the temperature is allowed to rise to room temperature. After being stirred for 5 hours, the reaction mixture is poured into 2 volumes of a mixture of water and ice (50/50); after 15 minutes, 1 volume of methylene chloride is added and the organic phase is separated. The latter is washed with an aqueous solution of $NaHCO_3$ (6% wt/v), then with water and dried over $MgSo_4$. After removal of the solvents by distillation at about 70° C., the residual oil is purified by distillation under reduced pressure. B.p.= 116–124° C./1 Pa. 29.8 g of ketone, which melts at 56°–58° C., are obtained.

M) 1-(2,4-dimethyl 6-methoxy)phenyl 2-bromo ethanone
(VII: $Ar_1$=2,4-$(CH_3)_2$-6-$(OCH_3)$—$C_6H_2$; $R_3$=H; X=Br)

i) 2.9 g of acetyl chloride are introduced into a mixture of 3,5-dimethyl anisole and 4.9 g of anhydrous aluminium chloride in 50 ml of 1,2-dichloroethane at a temperature lower than 10° C. After being stirred for 3 to 4 hours at room temperature, the reaction mixture is poured into 2 volumes of a water/ice mixture. One volume of methylene chloride is then added and the organic phase is separated. The latter is dried, then concentrated under reduced pressure at a temperature of about 60° C. The residual oil is purified by distillation under reduced pressure. B.p.=81° C./50 Pa.

ii) This ketone is brominated by $CuBr_2$ by using the procedure in K. M.p.=68° C.

N) 1-(3,5-ditert.butyl-4-hydroxy)phenyl 3-methyl 2-bromo butanone

This ketone is obtained according to the process M starting from isovaleryl chloride; M.p.=110° C.; The intermediate hydroxylated ketone melts at 109° C.

O) 3,5-dimethyl 4-(2-bromo 1-oxoethyl)acetanilide
(VII): $Ar_1$=3,5-$(CH_3)_2$ 4-(NH—$COCH_3$)—$C_6H_2$; $R_3$=H; X=Br)

6.24 g of phenyltrimethylammonium tribromide dissolved in 40 ml of tetrahydrofuran are introduced slowly at about 5° C. into a solution of 3.4 g of 3,5-dimethyl 4-acetyl acetanilide prepared according to the method described in J. Org. Chem. 18, 496–500 (1963), in 40 ml of tetrahydrofuran.

After 30 minutes at about 5° C., 3 ml of an aqueous solution of sodium hydrogen sulfite (0.5%-wt./v) and 30 ml of water are added at 20° C. The organic phase is separated and the aqueous phase is extracted with 30 ml of ethyl ether. The solvents are evaporated from the pooled organic phases; in this way, 3 g of the desired product melting at 142° C. are isolated.

P) 3,5-dimethyl 4-(2-bromo 1-oxoethyl)benzonitrile
(VII: $Ar_1$=3,5-$(CH_3)_2$ 4-(CN)—$C_6H_2$; $R_3$=H; X=Br)

4.6 g of bromine are introduced slowly at about −5° C. into a solution of 4 g of 4-acetyl 3,5-dimethyl benzonitrile, prepared according to the method described in J. Chem. Soc. Perkin Trans. II, p. 943–949 (1988), in 10 ml of diethyl ether and 5 ml of dioxane. The mixture is allowed to attain room temperature, and after it has been stirred for 1 hour 15 ml of a saturated solution of ammonium chloride are added to it. The organic phase is separated and the solvent is removed under reduced pressure to give 4.8 g of the desired product. M.p.=76° C.

The alpha-bromo ketones in Table 3, prepared according to one of the preceding procedures, were isolated, the others were used in the crude state.

TABLE 3

$Ar_1$—CO—CHBr—$R_3$

| $Ar_1$ | $R_3$ | Process | Physical constant |
|---|---|---|---|
| Cl—C₆H₄— | $CH_3$ | I | M.p. = 77° C. |
| 2-CH₃-C₆H₄— (with CH₃ substituent) | $CH_3$ | I | B.p. = 74° C./35 Pa |

TABLE 3-continued

| Ar₁ | R₃ | Process | Physical constant |
|---|---|---|---|
| 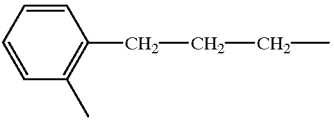 | —CH₂—CH₂—CH₂— | I | B.p. = 120° C./45 Pa |
| 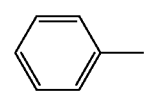 | n-C₆H₁₃ | J | B.p. = 110° C./1 Pa |
| 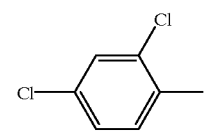 | H | J | M.p. < 50° C. |
| 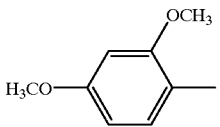 | H | J | M.p. = 80° C. |
| 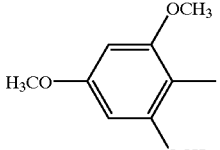 | H | J | M.p. = 76° C. |
| 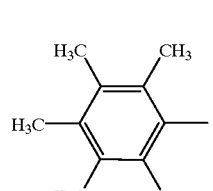 | H | J | M.p. = 110° C. |
| 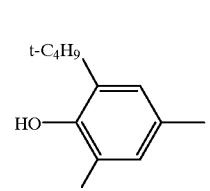 | H | J | M.p. = 140° C. |
| 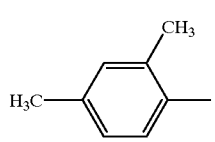 | H | K | B.p. = 60° C./15 Pa |
| 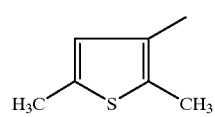 | H | J | M.p. = 65° C. |
| 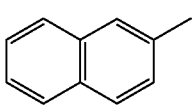 | H | O | M.p. = 83° C. |
| 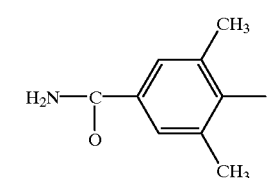 | H | P | M.p. = 145° C. |
| 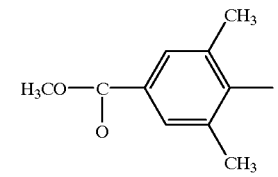 | H | P | M.p. = 117° C. |
| 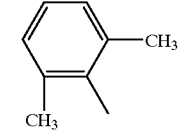 | H | P | M.p. < 30° C. |

Alpha-thiocyanato-ketones of Formula VIII

Q) 1-(2,4,6-trimethyl)phenyl 2-thiocyanato ethanone

A mixture of 7 g of anhydrous potassium thiocyanate, 16 g of 1-(2,4,6-trimethyl)phenyl 2-bromo ethanone and 180 ml of acetonitrile are maintained at about 50° C. for 3 hours. The precipitate formed is filtered off at about 15° C. and the filtrate is concentrated under reduced pressure. 250 ml of ethyl ether are added to the residue, the solid is separated and the ether removed. The residual oil is dissolved in isopropyl ether and the solution is cooled to 0° C. The precipitate formed is separated. 13.1 g of the desired product, which melts at 73° C., are thus obtained.

By applying this same procedure to 1-(2,4,6-triisopropyl)phenyl 2-bromo ethanone, 1-(2,4,6-triisopropyl)phenyl 2-thiocyanato ethanone is prepared, which melts at 86° C.

2-Halogen thiazoles of Formula V

R) 2-bromo 4-(2,4,6-triisopropylphenyl)thiazole

A solution of 2 g of 1-(2,4,6-triisopropyl)phenyl 2-thiocyanato ethanone in 80 ml of acetonitrile is cooled to 0° C. and hydrogen bromide is bubbled through the solution at this temperature to saturation. The mixture is then heated to 50° C. and maintained at this temperature for 2 hours in an atmosphere saturated with hydrogen bromide, then it is cooled to 10° C. and the precipitate formed is filtered off under a stream of nitrogen. 2.2 g of the hydrobromide of the expected compound are thus obtained. M.p.=236° C.

By applying the same procedure to 1-(2,4,6-trimethyl) phenyl 2-thiocyanato ethanone, 2-bromo 4-(2,4,6-trimethylphenyl) thiazole hydrobromide is obtained which melts at 270° C.

By introducing gaseous hydrogen chloride into the reaction mixture instead of hydrogen bromide, 2-chloro 4-(2,4,6-trimethylphenyl) thiazole hydrochloride is obtained which melts at 216° C.

2-Halogeno oxazoles of Formula V

S) 2-chloro 4-(2,4-dichlorophenyl)5-methyl oxazole i—2-hydroxy 1-(2,4-dichlorophenyl)propan-1-one 26.1 g of phenyl iodosoacetate are introduced into 150 ml of a solution of 15 g of 2,4-dichloropropiophenone in anhydrous methanol under an inert atmosphere, then 12.4 g of KOH in 60 ml of methanol are added at about 0° C. The reaction mixture is stirred at room temperature for 16 hours, then the solvent is evaporated under reduced pressure. The residue is taken up in 100 ml of water and 150 ml of methylene chloride; the organic phase is then separated, washed with water and the solvent is evaporated. 100 ml of a 5% aqueous solution of sulfuric acid (v/v) is added to the residue followed, after 20 min., by 100 ml of dichloromethane. The organic phase is separated and the solvent is removed under reduced pressure. The residue is chromatographed on silica by eluting with heptane, followed by a heptane/ethylacetate mixture (99/1 v/v). 7 g of the produce described and thus obtained.

ii—4-(2,4-dichlorophenyl)5-methyl oxazolin-2-one

Under an inert atmosphere, a solution of 3.6 ml of trichloromethyl chloroformate in 20 ml of anhydrous toluene is introduced into a solution of 6 g of the hydroxyketone obtained in i) and 8.2 ml of dimethylaniline in 80 ml of anhydrous toluene at about −50° C. After being stirred at this temperature for 1 hour, the mixture is allowed to attain room temperature and maintained there for 5 hours. Gaseous $NH_3$ is then bubbled into the mixture for 1 hour, then it is stirred for 2 hours before the precipitate is removed. The organic phase is washed with water, dried and concentrated under reduced pressure to a volume of about 20 ml. The precipitate formed is isolated, then purified by chromatography on silica by eluting with a mixture of isopropyl ether and heptane (8/2 v/v). 3.1 g of the desired product, which melts at 170° C., are thus isolated.

iii—2-chloro 4-(2,4-dichlorophenyl) 5-methyl oxazole 3 g of oxazolinone, obtained in ii, are dissolved in 15 ml of phosphorus oxychloride. 1.75 ml of triethylamine are added to this solution at 0° C., then the mixture is maintained at its reflux temperature for 6 hours. The volatile products are then distilled under reduced pressure and the residue is neutralized by the addition of a saturated aqueous solution of sodium bicarbonate at about 10° C. The aqueous phase is extracted 3 times with 80 ml of ethyl acetate; the pooled organic phases are concentrated to give 2.8 g of the expected product which melts at 78° C.

4-(4-methylphenyl) 5-methyl oxazolin-2-one, which melts at 169° C. and 2-chloro 4-(4-methylphenyl) 5-methyl oxazole, which melts below 50° C., are prepared according to the same procedures.

5-chloro thiadiazoles of Formula V

T) 5-chloro 3-(2,4,6-trimethylphenyl)1,2,4-thiadiazole i—2,4,6-trimethyl benzamidine 5 g of 2,4,6-trimethyl benzonitrile and 2.68 g of sodium amide in 80 ml of toluene are heated slowly to 100° C. under an inert atmosphere, then the mixture is allowed to attain room temperature and left at this temperature for about 16 hours. 10 ml of ethanol, then 100 ml of water and 200 ml of ethyl acetate are then introduced into the mixture, cooled to about 10° C.

The organic phase is separated, the solvent is evaporated under reduced pressure and the residue is purified by chromatography on silica by eluting with methylene chloride followed by a mixture of 25% (wt/v) aqueous solution of $NH_4OH$ with methanol (2/8 v/v). 2 g of amidine melting at 178° C. are thus obtained.

ii—5-chloro 3-(2,4,6-trimethylphenyl)1,2,4-thiadiazole 2.2 g of trichloromethanesulfenyl chloride are introduced into a solution of 2 g of 2,4,6-trimethyl benzamidine in 16 ml of dichloromethane under an inert atmosphere at about −20° C., followed by the slow addition of 2 g of NaOH dissolved in 3.2 ml of water at about −10° C. After 1 hour at about −5° C., the precipitate formed is isolated and the organic phase is separated and washed with 6 ml of water. After being dried over $K_2CO_3$, it is concentrated under reduced pressure to give 2.8 g of the desired product in the form of an oil, which may be used without purification.

5-chloro oxadiazoles of Formula V

U) 5-chloro 3-(2,4-dimethylphenyl) 1,2,4-oxadiazole i—2,4-dimethyl benzamidoxime 25 g of 2,4-dimethyl benzonitrile, 14.6 g of hydroxylamine hydrochloride, 29 g of potassium carbonate in 150 ml of ethanol and 35 ml of water are refluxed for 16 hours. Then 7.3 g of hydroxylamine hydrochloride are added followed by 14.5 g of potassium carbonate and reflux is continued for 5 hours.

The mixture is then concentrated to 70 ml by evaporation under reduced pressure, and to it are added 100 ml of water and 100 ml of methylene chloride. The organic phase is separated and the aqueous phase is reextracted twice with 100 ml of methylene chloride. The solvent is removed from the 3 pooled organic solutions by distillation under reduced pressure, then the residue is purified by chromatography on a column of silica by eluting with mixtures of cyclohexane and ethyl acetate (95/5 v/v, then 50/50 v/v). In this way, 17 g of a solid are isolated which, after recrystallization from ethyl acetate, melts at 150° C.

ii—3-(2,4-dimethylphenyl)1,2,4-oxadiazolin-5-one

Under an inert atmosphere, 10.5 g of 2,4-dimethyl benzamidoxime are dissolved in 40 ml of anhydrous toluene; 6.5 ml of pyridine and 7.6 g of ethyl chloroformate are added.

The mixture is maintained at its reflux temperature for 5 hours and the precipitate formed on cooling to room temperature is isolated, then redissolved in a mixture of 100 ml of water and 100 ml of ethyl acetate; after stirring and decantation, the organic phase is separated and concentrated under reduced pressure. In this way, 7.6 g of the expected product which melts at 170° C. are isolated.

iii—5-chloro 3-(2,4-dimethylphenyl) 1,2,4-oxadiazole 2 g of the product obtained in ii with 0.5 ml of pyridine, 0.5 ml of dimethylformamide and 15 ml of phosphorus oxychloride are maintained for 24 hours at about 100° C. The mixture is cooled and poured into 50 g of ice and the aqueous phase formed is extracted 3 times with 50 ml of ethyl ether. The organic phases are pooled, washed with water, dried and concentrated under reduced pressure. The residue dissolved in a heptane/ethyl acetate mixture (90/10 v/v) is filtered through silica. After evaporation of the solvent, 1.3 g of the expected compound, which melts at 54° C., is isolated.

In the following, examples of the implementation of the invention are described; the NMR spectra have been recorded at 250 MHz, unless indicated otherwise; the chemical shifts are expressed in ppm with respect to tetramethylsilane (substitution method); the melting points are instant melting points.

EXAMPLE 1

2-(N-[2-(1-pyrrolidinyl)ethyl] N-[1-(3-pyridyl)ethyl])amino 4-(2,4,6-trimethylphenyl)thiazole (formula I: A=S; B=C; $Ar_1$=2,4,6-$(CH_3)_3$—$C_6H_2$; $R_3$=H; $Ar_2$=3-pyridyl; $Z_1$=$(CH_2)_2$; $Z_2$=CH—$CH_3$; W=1-pyrrolidinyl)

2.4 g of N-[2-(1-pyrrolidinyl)ethyl] N-[1-(3-pyridyl)ethyl]thiourea, 2.04 g of 1-(2,4,6-trimethylphenyl) 2-bromo ethanone and 0.3 ml of an approximately 12N aqueous solution of HCl in 60 ml of ethanol are maintaind at about 70° C. under an inert atmosphere for about 15 hours. The mixture is then concentrated by distillation under reduced pressure and 50 ml of a 1N aqueous solution of HCl is added to the residue. After the aqueous phase has been washed twice with 20 ml of methylene chloride, a 4N aqueous solution of NaOH is added to give pH 8. It is then extracted 3 times with 50 ml of methylene chloride and, after being dried, the organic extracts are concentrated.

The residual oil (3.7 g) is purified by medium pressure chromatography on a column of silica by eluting with a mixture of ethyl acetate and methanol (50/50, then 30/70 v/v). 3.05 g of the desired product are thus obtained in the form of an oil.

$NMR^1H$(DMSOd6)amine: δ=8.58(m, 1H); 8.49(m, 1H); 7.77(m, 1H); 7.38(m, 1H); 6.86(s, 2H); 6.51(s, 1H); 5.40(q, 1H); 3.42(m, 2H); 2.65(m, 1H); 2.37(m, 5H); 2.23(s, 3H); 2.03(s, 6H); 1.63(m, 7H).

The hydrochloride of this compound is prepared by adding 11 ml of a 2N solution of HCl in $CH_3COOC_2H_5$ to a solution of 2.85 g of the oil in 2 ml of anhydrous methanol. The salt is isolated after removal of the solvents under reduced pressure. After drying at 50° C. under 0.1 Pa, 3.57 g of the trihydrochloride monohydrate are isolated. M.p.=155° C.

EXAMPLE 2

2-(N-[2-N',N'-dimethylaminoethyl] N-[3-pyridylmethyl])amino 4-(2,4,6-triisopropropyl phenyl) thiazole (formula I: A=S; B=C; $Ar_1$=2,4,6-/$CH(CH_3)_2/_3$—$C_6H_2$; $R_3$=H; $Ar_2$=3-pyridyl; $Z_1$=$(CH_2)_2$; $Z_2$=$CG_2$; W=$N(CH_3)_2$)

9.8 g of 1-(2,4,6-triisopropyl phenyl) 2-bromo ethanone, 5 g of N-[3-pyridylmethyl]N-[2-N',N'-dimethylaminoethyl] thiourea in 100 ml of anhydrous ethanol are maintained at the reflux temperature under an inert atmosphere for about 20 hours. The volatile products are then distilled under reduced pressure and 100 ml of a 2N aqueous solution of NaOH are added to the residue; the aqueous phase is extracted 3 times with 100 ml of methanol chloride and, after being washed with water and dried, the organic extracts are concentrated under reduced pressure. The residual oil is dissolved in about 50 ml of a methylene chloride/methanol mixture (9/1 v/v) and filtered through silica. The filtrate is evaporated to dryness and the residue is dissolved in 30 ml of acetone and mixed with 50 ml of a 1M solution of oxalic acid in acetone. The precipitate formed is isolated after 30 minutes. The dioxalate of the final product is thus obtained. M.p.=156–158° C.

The free amine functions are regenerated by reaction of NaOH on an aqueous solution of the dioxalate. The product crystallizes from petroleum ether. M.p.=84° C.

$NMR^1H$(DMSOd6)amine: δ=8.55(s, 1H); 8.47(m, 1H); 7.7(m, 1H); 7.33(m, 1H); 7.00(s, 2H); 6.51(s, 1H); 4.74(s, 2H); 3.54(m, 2H); 2.87(m, 1H); 2.71(m, 2H); 2.48(m, 2H); 2.15(s, 6H); 1.22(d, 6H); 1.06(d, 12H).

The monofumarate may be prepared by reaction of 1.2 equivalents of fumaric acid with a 10% solution (wt/v) of the base in isopropanol. M.p.=195° C.

The monomethane sulfonate, which crystallizes with 2 molecules of water, may be prepared in a mixture of ethyl ether and isopropanol (10/1, v/v). M.p.=180° C.

The trimaleate prepared in an ethyl ether/acetone mixture (2/7, v/v) melts at 115° C.

The trihydrochloride, which crystallizes with 3 molecules of water, may be prepared in ethyl ether. M.p.=140° C.

The compounds of formula I in which A=S, B=C of the examples 3 to 63 which appear in Table 4 were prepared by applying one of the preceding procedures. The characteristics of the NMR spectra of these compounds are shown in Table 6 below.

TABLE 4

| Ex. | $R_3$ | $Ar_1$ | —$Z_2$—$Ar_2$ | —$Z_1$—W | amine or salt of | M.p. ° C. |
|---|---|---|---|---|---|---|
| 3 | H | 2,4-dichloro-methylphenyl | —$CH_2$—(3-pyridyl) | —$(CH_2)_2$—$N(CH_3)_2$ | $2(COOH)_2$ | 182° C. |
| 4 | H | 2,6-dichloro-methylphenyl | —$CH_2$—(3-pyridyl) | —$(CH_2)_2$—$N(CH_3)_2$ | $2(COOH)_2$ | 165° C. |

TABLE 4-continued
| Ex. | R₃ | Ar₁ | —Z₂—Ar₂ | —Z₁—W | amine or salt of | M.p. ° C. |
|---|---|---|---|---|---|---|
| 5 | H | 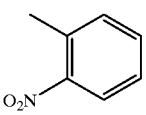 | 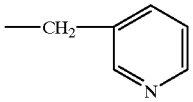 | —(CH₂)₂—N(CH₃)₂ | 2(COOH)₂ | 182° C. |
| 6 | H | 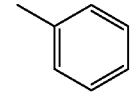 | 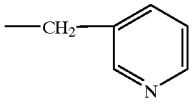 | —(CH₂)₂—N(CH₃)₂ | 1.5(COOH)₂ 2H₂O | 150° C. |
| 7 | H | 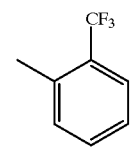 | 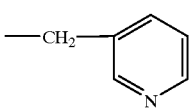 | —(CH₂)₂—N(CH₃)₂ | 2(COOH)₂ | 131° C. |
| 8 | CH₃ | 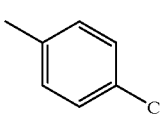 | 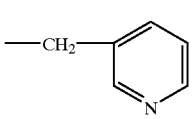 | —(CH₂)₂—N(CH₃)₂ | 3(COOH)₂ | 176° C. |
| 9 | CH₃ | 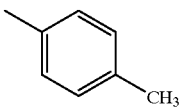 | 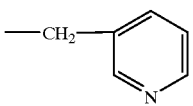 | —(CH₂)₂—N(CH₃)₂ | 2(COOH)₂ H₂O | 170° C. |
| 10 | H | 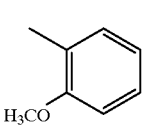 | 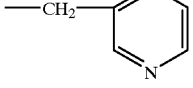 | —(CH₂)₂—N(CH₃)₂ | fumaric acid | 128° C. |
| 11 | H | 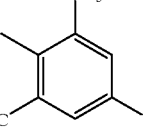 | 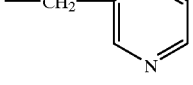 | —(CH₂)₂—N(CH₃)₂ | (COOH)₂ 4H₂O | 138° C. |
| 12 | |  |  | —(CH₂)₂—N(CH₃)₂ | fumaric acid 0.5H₂O | 162° C. |
| 13 | CH₃ | 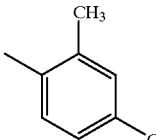 | 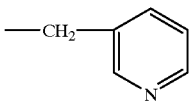 | —(CH₂)₂—N(CH₃)₂ | 1.5(COOH)₂ | 154° C. |
| 14 | H | 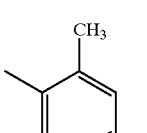 | 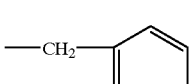 | —(CH₂)₂—N(CH₃)₂ | 3HCl, 3H₂O | 215– 220° C. |

TABLE 4-continued

| Ex. | R₃ | Ar₁ | —Z₂—Ar₂ | —Z₁—W | amine or salt of | M.p. ° C. |
|---|---|---|---|---|---|---|
| 15 | H | 2,3-dimethyl-5-methoxyphenyl (CH₃, CH₃, OCH₃ substituted benzene) | —CH₂—(3-pyridyl) | —(CH₂)₂—N(CH₃)₂ | fumaric acid | 178° C. |
| 16 | H | 2-methyl-3,4,6-trimethoxyphenyl | —CH₂—(3-pyridyl) | —(CH₂)₂—N(CH₃)₂ | fumaric acid | 147° C. |
| 17 | H | 2,3,4,6-tetramethylphenyl | —CH₂—(3-pyridyl) | —(CH₂)₃—N(CH₃)₂ | 3HCl, 2.5H₂O | 130–135° C. |
| 18 | H | 2,3,4,6-tetramethylphenyl | —CHCH₃—(3-pyridyl) | —(CH₂)₂—N(CH₃)₂ | 3HCl, 2H₂O | 190–195° C. |
| 19 | H | 2,3,4,6-tetramethylphenyl | —CHCH₃—(3-pyridyl) | —(CH₂)₂—N(CH₃)₂ | 3HCl, 3H₂O | 188–190° C. |
| 20 | H | 2,3,4,6-tetramethylphenyl | —CH₂—(3-pyridyl) | —CH(CH₃)—CH₂—N(CH₃)₂ | 2(fumaric acid) | 168° C. |
| 21 | H | 2,3,4,6-tetramethylphenyl | —CH₂—(3-pyridyl) | —CH₂—(2-pyridyl) | 3HCl, H₂O | 138° C. |
| 22 | H | 2,3,4,6-tetramethylphenyl | —CH₂—(3-pyridyl) | —CH₂—(3-pyridyl) | 3HCl, 2H₂O | 210° C. |
| 23 | H | 2,3,4,6-tetramethylphenyl | —CH₂—(3-pyridyl) | —(CH₂)₃—(1-imidazolyl) | 3HCl, 2.5H₂O | 140–150° C. |

TABLE 4-continued

| Ex. | R$_3$ | Ar$_1$ | —Z$_2$—Ar$_2$ | —Z$_1$—W | amine or salt of | M.p. ° C. |
|---|---|---|---|---|---|---|
| 24 | H | 2,3,5-trimethylphenyl | —CH$_2$-(3-pyridyl) | —(CH$_2$)$_2$-morpholino | 1.5(fumaric acid) | 151° C. |
| 25 | H | pentamethylphenyl | —CH$_2$-(3-pyridyl) | —(CH$_2$)$_2$—N(CH$_3$)$_2$ | fumaric acid H$_2$O | 166° C. |
| 26 | H | 2,3,5-trimethylphenyl | —CH$_2$-(3-pyridyl) | —(CH$_2$)$_2$—N(C$_2$H$_5$)$_2$ | 3HCl, 2.5H$_2$O | 170–180° C. |
| 27 | H | 2,3,5-trimethylphenyl | —CHCH$_3$-(3-pyridyl) | —(CH$_2$)$_3$—N(CH$_3$)$_2$ | HCl, 3.5H$_2$O | 135° C. |
| 28 | H | 2,3,5-trimethylphenyl | —CHCH$_3$-(3-pyridyl) | —(CH$_2$)$_3$-imidazolyl | 1.5(+)tartaric acid 5H$_2$O | 90° C. |
| 29 | H | 2,3,5-trimethylphenyl | —CH$_2$-(3-pyridyl) | —(CH$_2$)$_3$-morpholino | 1.5 fumaric acid 0.5H$_2$O | 81° C. |
| 30 | H | 2,3,5-trimethylphenyl | —CHCH$_3$-(3-pyridyl) | —(CH$_2$)$_2$—N(C$_2$H$_5$)$_2$ | 3HCl, 2H$_2$O | 182–186° C. |
| 31 | —C$_6$H$_{13}$ | phenyl | —CH$_2$-(3-pyridyl) | —(CH$_2$)$_2$—N(CH$_3$)$_2$ | 3HCl, 2H$_2$O | |

TABLE 4-continued

| Ex. | R₃ | Ar₁ | —Z₂—Ar₂ | —Z₁—W | amine or salt of | M.p. ° C. |
|---|---|---|---|---|---|---|
| 32 | H | 2,3,5-trimethylphenyl | —CHCH₃-(3-pyridyl) | —CHCH₃-(3-pyridyl) | amine | 168° C. |
| 33 | H | 2,3,5-trimethylphenyl | —CHCH₃-(3-pyridyl) | —(CH₂)₂-morpholinyl | 1.5 (fumaric acid) H₂O | 148° C. |
| 34 | H | 2,3,5-trimethylphenyl | —CHCH₃-(3-pyridyl) | —CH₂-(1-ethylpyrrolidin-2-yl) | 2HCl, H₂O | 89° C. |
| 35 | H | 2,3,5-trimethylphenyl | —CHCH₃-(3-pyridyl) | —(CH₂)₂-piperidinyl | 3HCl, 2H₂O | 100–110° C. |
| 36 | H | 2,3,5-trimethylphenyl | —CH₂-(3-pyridyl) | —(CH₂)₂—N(i-C₃H₇)₂ | 3HCl, 1.5H₂O | 120° C. |
| 37 | H | 2,3,5-trimethylphenyl | —CHCH₃-(3-pyridyl) | —(CH₂)₂—N(i-C₃H₇)₂ | 3HCl, 2H₂O | — |
| 38 | H | 3,5-di-tert-butylphenyl | —CH₂-(3-pyridyl) | —(CH₂)₂—N(CH₃)₂ | fumaric acid | 164° C. |
| 39 | H | 3,5-di-tert-butyl-4-hydroxyphenyl | —CH₂-(3-pyridyl) | —(CH₂)₂—N(CH₃)₂ | amine | 140° C. |
| 40 | H | 2,3,5-trimethylphenyl | —CHCH₃-(3-pyridyl) | —(CH₂)₂—N(C₄H₉)₂ | 3HBr, 1.5H₂O | 151° C. |

TABLE 4-continued
| Ex. | R₃ | Ar₁ | —Z₂—Ar₂ | —Z₁—W | amine or salt of | M.p. °C. |
|---|---|---|---|---|---|---|
| 41 | H | 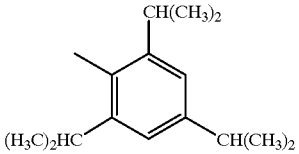 | 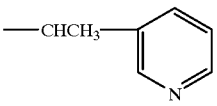 | —(CH₂)₂—N(CH₃)₂ | 3HCl, 2H₂O | 140° C. |
| 42 | H | 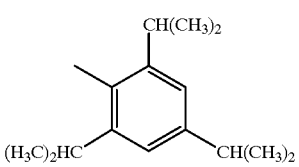 | 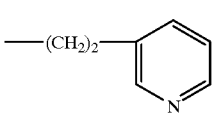 | —(CH₂)₂—N(CH₃)₂ | amine | 110° C. |
| 43 | H | 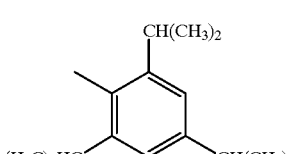 | 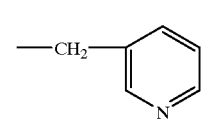 | —(CH₂)₃—N(CH₃)₂ | 2(COOH)₂ 0.5H₂O | 144° C. |
| 44 | H | 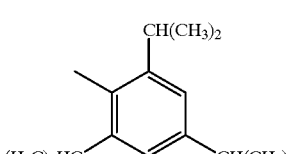 | 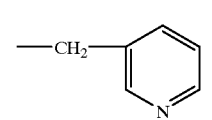 | 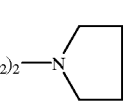 | amine 0.5H₂O | 97° C. |
| 45 | H | 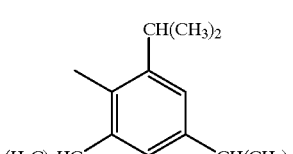 | 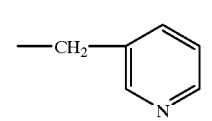 | 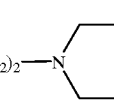 | 2(COOH)₂, 0.5H₂O | 110° C. |
| 46 | H | 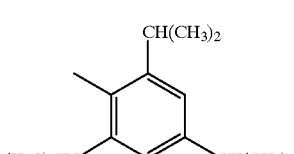 | 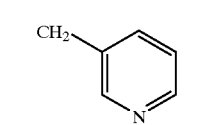 | 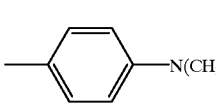 | 2(COOH)₂, 1H₂O | 156 158 |
| 47 | H | 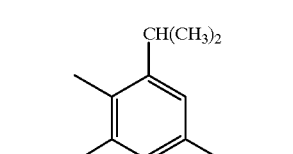 | 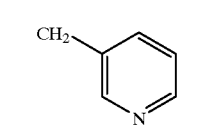 | —(CH₂)₄—N(CH₃)₂ | 2(COOH)₂, | 148 |
| 48 | H | 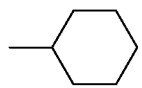 | 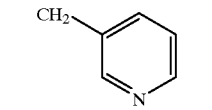 | —(CH₂)₂—N(CH₃)₂ | 2(COOH)₂, H₂O | 122 |
| 49 | H | 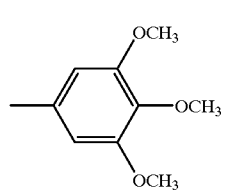 | 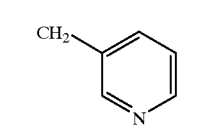 | —(CH₂)₂—N(CH₃)₂ | 2(COOH)₂ | 152 |

TABLE 4-continued
| Ex. | R₃ | Ar₁ | —Z₂—Ar₂ | —Z₁—W | amine or salt of | M.p. °C. |
|---|---|---|---|---|---|---|
| 50 | CH₃ | 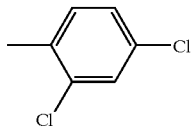 | 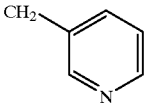 | —(CH₂)₂—N(CH₃)₂ | (COOH)₂, 0.5H₂O | 186 |
| 51 | CH(CH₃)₂ | 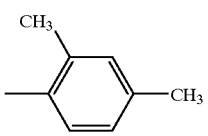 | 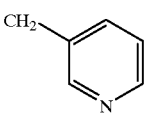 | —(CH₂)₂—N(CH₃)₂ | 2(COOH)₂, H₂O | 88 |
| 52 | H | 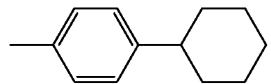 | 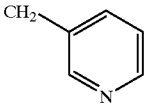 | —(CH₂)₂—N(CH₃)₂ | — | 72 |
| 53 | H | 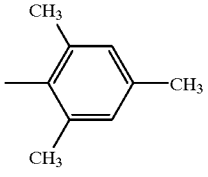 | 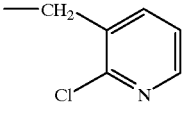 | —(CH₂)₂—N(CH₃)₂ | 1.5(COOH)₂, 0.75H₂O | 121 |
| 54 | H | 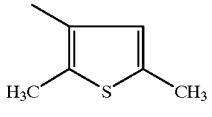 | 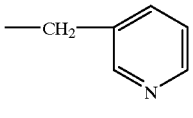 | —(CH₂)₂—N(CH₃)₂ | (COOH)₂, 0.5H₂O | 179 |
| 55 | H | 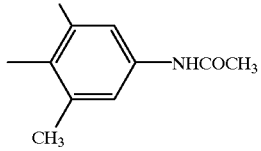 | 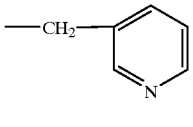 | —(CH₂)₂—N(CH₃)₂ | 2(COOH)₂, 1.5H₂O | 98 |
| 56 | H | 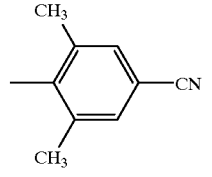 | 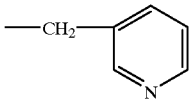 | —(CH₂)₂—N(CH₃)₂ | (COOH)₂ 1H₂O | 200 |
| 57 | H | 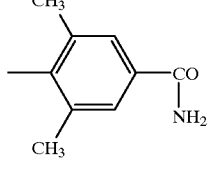 | 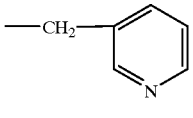 | —(CH₂)₂—N(CH₃)₂ | 2(COOH)₂, 0.5C₃H₇OH | 145 |
| 58 | H | 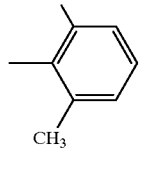 | 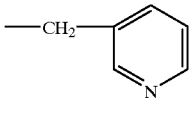 | —(CH₂)₂—N(CH₃)₂ | 2(COOH)₂ | 152 |

TABLE 4-continued

| Ex. | R₃ | Ar₁ | —Z₂—Ar₂ | —Z₁—W | amine or salt of | M.p. °C. |
|---|---|---|---|---|---|---|
| 59 | H | 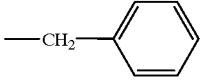 | 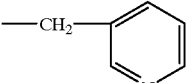 | —(CH₂)₂—N(CH₃)₂ | 2(COOH)₂, 0.5H₂O | 135 |
| 60 | CH(CH₃)₂ | 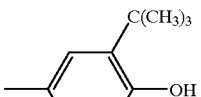 | 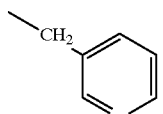 | —(CH₂)₂—N(CH₃)₂ | 3HCl, 4H₂O | 180–200 |
| 61 | H | 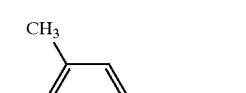 | 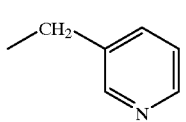 | —(CH₂)₂—N(CH₃)₂ | 2(COOH)₂ | 130 |
| 62 | H |  | 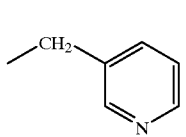 | —(CH₂)₂—N(CH₃)₂ | (COOH)₂, 0.75H₂O | 145 |
| 63 | H | 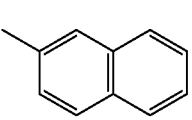 | 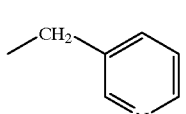 | —(CH₂)₂—N(CH₃)₂ | (COOH)₂ | 158 |

EXAMPLE 64

2-(N-[2-piperidino ethyl]N-[3-pyridylmethyl]amino) 4-(2,4,6-trimethylphenyl)thiazole (formula I: A=S; B=C, Ar₁=2,4,6-(CH₃)₃—C₆H₂; R₃=H; Ar₂=3-pyridyl; Z₁=(CH₂)₂; Z₂=CH₂; W=piperidino).

2.3 g of 1-(2,4,6-trimethylphenyl) 2-thiocyanato ethanone and 2.1 g of N-piperidino N'-[3-pyridylmethyl]ethane diamine in 40 ml of anhydrous toluene are maintained at 50° C. for 48 hours. The organic phase is extracted with 50 ml of a 1N aqueous solution of HCl at room temperature; after being washed twice with 20 ml of methylene chloride, the aqueous phase is brought to pH 8 by the addition of a 10N aqueous solution of NaOH, then extracted 3 times with 30 ml of methylene chloride. The organic extracts are concentrated after being dried and the residual oil is purified by chromatography on a column of silica by eluting with ethyl ether, followed by a methylene chloride/methanol mixture (96/4, v/v).

The final product is an oil, the oxalate of which is prepared by reaction of 0.65 g of oxalic acid dihydrate with 1.08 g of oil in 35 ml of acetone. In this way, the salt monohydrate is isolated which contains 2 molecules of acid for one of the product of formula I and which melts at 100° C.

NMR¹H (DMSOd6) salt: δ=8.53(m, 2H); 7.75(m, 1H); 7.40(m, 1H); 6.68(s, 2H); 6.63(s, 1H); 4.73(m, 2H); 3.91(m, 2H); 3.31(m, 2H); 3.16(m, 4H); 2.34(s, 3H); 2.06(s, 6H); 1.61(m, 4H); 1.46(m, 2H).

EXAMPLE 65

2-(N-[2-(N'-tert.butoxycarbonyl N'-methyl) aminoethyl]N-[3-pyridylmethyl]amino) 4-(2,4,6-triisopropylphenyl) thiazole (formula I: A=S; B=C; Ar₁=2,4,6-/CH(CH₃)₂/₃—C₆H₂; R₃=H; Ar₂=3-pyridyl; Z₁=(CH₂)₂; Z₂=CH₂; W=N(CH₃)COOC(CH₃)₂.

4.2 g of N-(tert.butoxycarbonyl N-methyl) N'-[3-pyridylmethyl]ethanediamine and 4.8 g of 1-(2,4,6-triisopropylphenyl) 2-thiocyanato ethanone in 50 ml of toluene are maintained at 65° C. for 72 hours. The solvent is then removed under reduced pressure and the residual oil is purified by chromatography on a column of silica by eluting first with a mixture of ethyl ether and methylene chloride (50/50 v/v) and finally, with methylene chloride. 4.53 g of the expected product are thus isolated in the form of an oil.

NMR¹H (CDCl₃)amine: δ=8.59(m, 2H); 7.66(m, 1H); 7.25(m, 1H); 7.03(s, 2H); 6.27(s, 1H); 4.77(m, 2H); 3.50(m, 4H); 2.87(s, 3H); 2.9–2.74(m, 3H); 1.44(s, 9H); 1.26(d, 6H); 1.14(d, 12H).

EXAMPLE 66

2-(N-[2-(N'-methylaminoethyl) N-[3-pyridylmethyl] amino)4-(2,4,6-triisopropylphenyl) thiazole (formula I: A=S; B=C; Ar₁=2,4,6-[CH(CH₃)₂]₃—C₆H₂; R₃=H; Ar₂=3-pyridyl; Z₁=(CH₂)₂; Z₂=CH₂; W=NHCH₃).

Under an inert atmosphere, 1.9 g of the previous compound are dissolved in 20 ml of anhydrous ethyl acetate and 5 ml of anisole and 20 ml of a 5N solution of HCl in ethyl acetate are added slowly at 5° C. The mixture is allowed to attain room temperature and after being stirred for 2 hours is cooled to about 5° C. before a 5N aqueous solution of NaOH is added to give a basic pH. The organic phase is then separated, dried and concentrated at about 70° C. under reduced pressure. The residual oil is dissolved in 60 ml of isopropanol and decolorized by means of 50 mg of active charcoal and 50 ml of a 0.5M solution of oxalic acid dihydrate in isopropanol are added; the precipitated salt is isolated by filtration. 1.5 g of oxalate hemihydrate are thus obtained (containing two molecules of oxalic acid), M.p.=130° C.

NMR$^1$H (DMSOd6) salt: δ=8.53(m, 2H); 7.72(m, 1H); 7.39(m, 1H); 7.02(s, 2H); 6.63(s, 1H); 4.75(m, 2H); 3.75(t, 2H); 3.22(t, 2H); 2.86(s, 1H); 2.71(s, 2H); 2.58(s, 3H); 1.21(d, 6H); 1.08(d, 12H).

EXAMPLE 67

2-(N-[2-(N'-tert.butoxycarbonyl)amino ethyl]N-[3-pyridylmethyl]amino) 4-(2,4,6-triisopropylphenyl)thiazole (formula I: A=S; B=C; Ar$_1$=2,4,6-[CH(CH$_3$)$_2$]$_3$—C$_6$H$_2$; R$_3$=H; Ar$_2$=3-pyridyl; Z$_1$=(CH$_2$)$_2$; Z$_2$=CH$_2$; W=NHCOOC(CH$_3$)$_3$).

This product is prepared by applying the method used in example 65 starting from N-[tert.butoxycarbonyl]N'-[3-pyridylmethyl]ethanediamine.

M.p.=55° C.

NMR$^1$H (DMSOd6) amine: δ8.50(m, 2H); 7.77(d, 1H); 7.33(m, 1H); 7.00(s, 3H); 6.54(s, 1H); 4.74(s, 2H); 3.43(m, 2H); 3.20(m, 2H); 2.86(m, 1H); 2.70(m, 2H); 1.37(s, 9H); 1.21(d, 6H); 1.05(d, 12H).

EXAMPLE 68

2-(N-[2-aminoethyl]N-[3-pyridylmethyl]amino)4-(2,4,6-triisopropylphenyl)thiazole (formula I: A=S; B=C; Ar$_1$=2,4,6-(CH(CH$_3$)$_2$)$_3$—C$_6$H$_2$; R$_3$=H; Ar$_2$=3-pyridyl; Z$_1$=(CH$_2$)$_2$; Z$_2$=CH$_2$; W=NH$_2$).

Compound prepared starting from that of example 67 by applying the method described in example 66.

The dioxalate hemihydrate melts at 187° C.

NMR$^1$H (DMSOd6) salt: δ=8.53(m, 2H); 8.2(s, 2H); 7.74(m, 1H); 7.38(m, 1H); 7.02(s, 2H); 6.62(s, 1H); 4.74(s, 2H); 3.71(m, 2H); 3.10(m, 2H); 2.89(m, 1H); 2.71(m, 2H); 1.21(d, 6H); 1.08(d, 12H).

The compounds of formula I of the examples 69 to 77, described in Table 5, for which A=S and B=C, were prepared by applying the procedures of the examples 64 to 66; the NMR spectra of these compounds are presented in Table 6.

TABLE 5

| Ex. | R$_3$ | —Z$_1$—W | Z$_2$—Ar$_2$ | Ar$_1$ | amine or salt of | M.p. ° C. |
|---|---|---|---|---|---|---|
| 69 | H | —(CH$_2$)$_2$—N(pyrrolidine) | —CH$_2$-(3-pyridyl) | 2,3,5-trimethylphenyl | 3(CF$_3$COOH) | |
| 70 | H | —(CH$_2$)$_2$N(N-CH$_3$-piperazine) | —CH$_2$-(3-pyridyl) | 2,3,5-trimethylphenyl | 2(COOH)$_2$ | 202° |
| 71 | H | —(CH$_2$)$_2$—N(CH$_3$)$_2$ | —CH$_2$-(3-quinolyl) | 2,3,5-trimethylphenyl | 1,5(+) tartaric acid | 110° |
| 72 | H | —(CH$_2$)$_2$—N(CH$_3$)$_2$ | —CH$_2$-(2-pyridyl) | 2-methyl-3,5-bis(isopropyl)phenyl | 2(COOH)$_2$ | 164° |

TABLE 5-continued

| Ex. | $R_3$ | —$Z_1$—W | $Z_2$—$Ar_2$ | $Ar_1$ | amine or salt of | M.p. °C. |
|---|---|---|---|---|---|---|
| 73 | H | —$(CH_2)_2$—$N(CH_3)_2$ | —$CH_2$-(1-methylindol-3-yl) | 2,3,5-trimethylphenyl | $(COOH)_2$, $H_2O$ | 155° |
| 74 | H | —$(CH_2)_2SC_2H_5$ | $CH_2$-(3-pyridyl) | 2,4,6-triisopropylphenyl | 2HCl, $H_2O$ | 145 |
| 75 | H | —$CH_2CON(CH_3)_2$ | $CH_2$-(3-pyridyl) | 2,3,5-trimethylphenyl | $2H_3PO_4C_3H_7OH$ | 140 |
| 76 | H | —$CH_2COOCH_3$ | $CH_2$-(3-pyridyl) | 2,4,6-triisopropylphenyl | — | oil |
| 77 | H | —$(CH_2)_2OCH_3$ | $CH_2$-(3-pyridyl) | 2,4,6-triisopropylphenyl | — | 94 |

EXAMPLE 78

2-(N-[2-(N'-methyl N'-phenylamino)ethyl]N-[3-pyridylmethyl]amino)4-(2,4,6-trimethylphenyl)thiazole, bromhydrate (formula I: A=S; B=C; $Ar_1$=2,4,6-$(CH_3)_3$—$C_6H_2$; $R_3$=H; $Ar_2$=3-pyridyl; $Z_1$=$(CH_2)_2$; $Z_2$=$CH_2$; W=$NCH_3C_6H_5$).

1 g of N-phenyl N-methyl N'-(3-pyridylmethyl) ethanediamine and 1.5 g of 2-bromo 4-(2,4,6-trimethylphenyl) thiazole in 50 ml of toluene are maintained at about 60° C. under an inert atmosphere for about 96 hours. The mixture is then concentrated under reduced pressure and 20 ml of a 1N aqueous solution of NaOH are added to the residue before it is extracted 3 times with 20 ml of methylene chloride. The organic extracts, washed and dried, are concentrated under reduced pressure and the residual oil is purified by chromatography on a column of silica by eluting with a mixture of methylene chloride and methanol (99/1 v/v). 1.1 g of final product are thus isolated in the form of an oil.

The trihydrochloride, prepared by reaction with HCl in ethyl ether, crystallizes with 1.5 molecules of water; it melts at 160° C.

NMR$^1$H (DMSOd6) salt: δ=8.84(m, 2H); 8.45(m, 1H); 7.97(m, 1H); 7.15(m, 2H); 6.85(m, 5H); 6.67(s, 1H); 4.92(s, 2H); 3.75(m, 4H); 2.92(s, 3H); 2.22(s, 3H); 1.98(s, 6H).

EXAMPLE 79

2-(N-[2-(N',N'-dimethylaminoethyl]N-[3-pyridylmethyl]amino)4-(2,4-dichlorophenyl)5-methyl oxazole (formula I: A=O; B=C; $Ar_1$=2,4-$(Cl)_2$—$C_6H_3$; $R_3$=$CH_3$; $Ar_2$=3-pyridyl; $Z_1$=$(CH_2)_2$; $Z_2$=$CH_2$; W=$N(CH_3)_2$).

A solution of 0.7 g of 2-chloro 4-(2,4-dichlorophenyl)5-methyl oxazole and 1.4 g of N-/2-dimethylaminoethyl/N-/3-pyridylmethyl/amine in 40 ml of anhydrous toluene is maintained at about 95° C. under an inert atmosphere for 80 hours. The solvent is then evaporated under reduced pressure, 3 ml of methanol and a saturated solution of sodium bicarbonate to give a basic pH in order to liberate the amine are added to the residue. The mixture is then concentrated under reduced pressure and the residue is purified by chromatography on a column of silica by eluting successively with ethyl ether, methylene chloride and a methylene chloride/methanol mixture (98/2 v/v).

0.45 g of the expected product is thus isolated in the form of an oil.

Its trihemioxalate /1.5(COOH)$_2$/, prepared by reaction with oxalic acid hydrate in isopropanol, crystallizes with 3H$_2$O. M.p.=130° C.

NMR$^1$H (DMSOd6) salt: δ=8.60(s, 1H); 8.53(m, 1H); 7.78(m, 2H); 7.44(m, 3H); 4.64(s, 2H); 3.7(t, 2H); 3.36(t, 2H); 2.82(s, 6H); 2.2(s, 3H).

EXAMPLE 80

2-(N-[2-(N',N'-dimethylaminoethyl]N-[3-pyridylmethyl]amino) 4-(4-methylphenyl) 5-methyl oxazole (formula I: A=O; B=C; Ar$_1$=4-(CH$_3$)—C$_6$H$_4$; R$_3$=CH3; Ar$_2$=3-pyridyl; Z$_1$=(CH$_2$)$_2$; Z$_2$=CH$_2$; W=N(CH$_3$)$_2$).

This compound was prepared by applying the process used in example 79.

The dioxalate, /2(COOH)$_2$/, crystallized with 1.5 H$_2$O melts at 180–190° C.

NMR$^1$H (DMSOd6) base: δ=8.55(m, 2H); 7.70(m, 1H); 7.45(m, 3H); 7.22(m, 2H); 4.66(s, 2H); 3.76(m, 2H); 3.38 (m, 2H); 2.86(s, 6H); 2.43(s, 3H); 2.32(s, 3H).

EXAMPLE 81

2-(N-[2-pyrrolidinoethyl]N-[3-pyridylmethyl]amino) 4-(2,4-dichlorophenyl) 5-methyl oxazole (formula I: A=O; B=C; Ar$_1$=4-(Cl)$_2$—C$_6$H$_3$; R$_3$=CH$_3$; Ar$_2$=3-pyridyl; Z$_1$=(CH$_2$)$_2$; Z$_2$=CH$_2$;

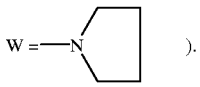

This compound is prepared by applying the process used in example 79.

The oxalate, crystallized with 4 H$_2$O, melts at 145° C.

NMR$^1$H (DMSOd6) salt: δ=8.5(m, 2H); 7.8(m, 2H); 7.4(m, 3H); 4.6(s, 2H); 4–3(m, 8H); 2.2(s, 3H); 1.9(m, 4H).

EXAMPLE 82

5-(N-[2-N',N'-dimethylaminoethyl]N-[2-(3-pyridyl)ethyl]amino) 3-(2,4,6-trimethylphenyl) 1,2,4-thiadiazole (formula I: A=S; B=N; Ar$_1$=2,4,6-(CH$_3$)$_3$—C$_6$H$_2$; R$_3$=nothing; Ar$_2$= 3-pyridyl; Z$_1$=(CH$_2$)$_2$; Z$_2$=CH$_2$; W=N(CH$_3$)$_2$).

0.45 g of 5-chloro 3-(2,4,6-trimethylphenyl) 1,2,4-thiadiazole and 1.2 g of N,N-dimethyl N'-[2-(3-pyridyl)ethyl]ethanediamine dissolved in 10 ml of ethanol are maintained under an inert atmosphere at about 55° C. for 7 hours, then 0.5 ml of a 1N aqueous solution of NaOH and 2 g of silica are added at room temperature. The mixture is concentrated to dryness and the residue is chromatographed on a column of silica by eluting successively with pure dichloromethane, then a dichloromethane/methanol mixture (98/2 v/v). 0.52 g of the desired product is thus obtained in the form of an oil.

The dioxalate, prepared in acetone and crystallized with 1H$_2$O, melts at 131° C.

NMR$^1$H (DMSOd6) salt: δ=8.45(m, 2H); 7.7(m, 1H); 7.3(m, 1H); 6.9(s, 2H); 3.9(m, 2H); 3.6(m, 2H); 3.3(m, 2H); 3(m, 2H); 2.8(s, 6H); 2.27(s, 3H); 2.09(m, 6H).

The compounds of the examples 83 to 86 were prepared by applying the procedure used in example 82.

EXAMPLE 83

5-(N-[2-N',N'-dimethylaminoethyl]N-[3-pyridylmethyl]amino) 3-(2,4,6-trimethylphenyl) 1,2,4-thiadiazole (formula I: A=S; B=N; Ar$_1$=2,4,6-(CH$_3$)$_3$—C$_6$H$_2$; R$_3$=nothing; ; Ar$_2$=3-pyridyl; Z$_1$=(CH$_2$)$_2$; Z$_2$=CH$_2$; W=N(CH$_3$)$_2$).

The salt with 1.5 molecules of oxalic acid, crystallized with 0.5 molecule of water and 0.5 molecule of acetone, melts at about 145° C.

EXAMPLE 84

5-(N-[2-N',N'-dimethylaminoethyl]N-[3-pyridylmethyl]amino) 3-phenyl 1,2,4-thiadiazole (formula I: A=S; B=N; Ar$_1$=C$_6$H$_5$; R$_3$=nothing; Ar$_2$=3-pyridyl; Z$_1$=(CH$_2$)$_2$; Z$_2$=CH$_2$; W=N(CH$_3$)$_2$).

The dioxalate of this compound melts at 173° C.

EXAMPLE 85

5(N-[methoxyethyl]N-[3-pyridylmethyl]amino) 3-(2,4,6-trimethylphenyl) 1,2,4-thiadiazole (formula I: A=S; B=N; Ar$_1$=2,4,6-(C$_3$)$_3$—C$_6$H$_2$; R$_3$=nothing; Ar$_2$ =3-pyridyl; Z$_1$=(CH$_2$)$_2$; Z$_2$=CH$_2$; W=OCH$_3$).

The dioxalate of this compound, crystallized with 1.5 H$_2$O, melts at 145° C.

EXAMPLE 86

5-(N-[2-N',N'-dimethylaminoethyl]N-[3-pyridylmethyl]amino) 3-(2,4-dimethylphenyl) 1,2,4-oxadiazole (formula I: A=O; B=N; Ar$_1$=2,4-(C$_3$)$_2$—C$_6$H$_3$; R$_3$=nothing; Ar$_2$=3-pyridyl; Z$_1$=(CH$_2$)$_2$; Z$_2$=CH$_2$; W=N(CH$_3$)$_2$).

0.5 g of 5-chloro 3-(2,4-dimethylphenyl) 1,2,4-oxadiazole and 1.3 g of N,N-dimethyl N'-[3-pyridylmethyl] ethanediamine in 20 ml of anhydrous toluene are stirred under an inert atmosphere for 16 hours at room temperature. The precipitate is removed by filtration and 10 ml of a 5% (wt/v) solution of ammonia are added to the filtrate; the organic phase is separated and the aqueous phase is re-extracted twice with 15 ml of ethyl acetate. The organic extracts are combined and concentrated under reduced pressure, and the residue is purified by chromatography on a column of silica by eluting with a mixture of methylene chloride and methanol (98/2 v/v). 0.6 g of the expected product is thus obtained in the form of an oil.

Its dioxalate, prepared in acetone, melts at 166° C.

NMR$^1$H (DMSOd6) salt: δ=8.62(m, 1H); 8.53(m, 1H); 7.7(m, 2H); 7.4(m, 1H); 7.16(m, 2H); 4.77(s, 2H); 3.9(t, 2H); 3.4(t, 2H); 2.82(s, 6H); 2.47(s, 3H); 2.31(m, 3H).

EXAMPLE 87

5-(N-[2-N',N'-dimethylaminoethyl]N-[2-pyridylmethyl]amino) 3-2,4-dimethylphenyl) 1,2,4-oxadiazole.

(formula I: A=O; B=N; Ar$_1$=2,4-(CH$_3$)$_2$—C$_6$H$_3$; R$_3$=nothing; Ar$_2$=2-pyridyl; Z$_1$=(CH$_2$)$_2$; Z$_2$=CH$_2$; W=N(CH$_3$)$_2$).

Prepared by applying the procedure described in example 86.

The oxalic acid salt, which contains 2.5 molecules of oxalic acid, melts at 148° C.

NMR$^1$H (DMSOd6) salt: δ=8.57(d, 1H); 7.88(t, 1H); 7.71(d, 1H); 7.49(d, 1H); 7.4(m, 1H); 7.14(m, 2H); 4.84(s, 2H); 4.0(t, 2H); 3.48(t, 2H); 2.9(s, 6H); 2.43(s, 3H); 2.3(s, 3H).

EXAMPLE 88

5-(N-[2-N',N'-dimethylaminoethyl]N-[3-pyridylmethyl]amino) 3-phenyl) 1,2,4-oxadiazole
(formula I: A=O; B=N; $Ar_1=C_6H_5$; $R_3$=nothing; $Ar_2$=3-pyridyl; $Z_1=(CH_2)_2$; $Z_2=CH_2$; $W=N(CH_3)_2$).

i—5-(N-[2-N',N'-dimethylaminoethyl]) amino 3-phenyl) 1,2,4-oxadiazole.

A mixture of 1.5 g of 5-trichloromethyl 3-phenyl 1,2,4-oxadiazole, prepared as described in Helv. Chem. Acta 46, 1067–1073 (1963) and 2.2 g of N,N-dimethylethane diamine is maintained at 35° C. for about 65 hours. The excess amine is removed by distillation under reduced pressure and 10 ml of a saturated aqueous solution of sodium bicarbonate are added to the residue; the aqueous phase is extracted 3 times with 10 ml of ethyl acetate and the pooled organic extracts are concentrated to dryness, after being washed with water and dried.

1.32 g of the expected product are thus isolated in the form of an oil.

ii—5-(N-[2-N',N'-dimethylaminoethyl]N-[3-pyridylmethyl]amino) 3-phenyl) 1,2,4-oxadiazole.

A mixture of 1 g of the product obtained in i), 0.78 g of 3-chloromethyl pyridine, 25 ml of methylene chloride and 20 ml of a 50% (wt/v) aqueous solution of NaOH is stirred for 16 hours.

The organic phase is then separated and the aqueous phase is re-extracted with one volume of methylene chloride. The pooled organic extracts are washed with water, dried and concentrated. The residue is chromatographed on silica by eluting successively with ethyl ether, methylene chloride and the mixture of methylene chloride/methanol (97/3 v/v). 0.8 g of the desired product is thus obtained.

The dioxalate (2(COOH)$_2$), prepared in acetone and crystallized with 0.5 H$_2$O, melts at 125° C.

NMR$^1$H (DMSOd6) salt: δ=8.65(s, 1H); 8.56(m, 1H); 7.9(m, 3H); 7.5(m, 4H); 4.80(s, 2H); 3.93(t, 2H); 3.42(t, 2H); 2.86(s, 6H).

EXAMPLE 89

N-oxide of the compound prepared in example 2
(formula I: A=S; B=C; $Ar_1=2,4,6-[CH(CH_3)_2]_3-C_6H_2$; $R_3$=H; $Ar_2$=3-pyridyl; $Z_1=(CH_2)_2$; $Z_2=CH_2$; $W=N(O)(CH_3)_2$).

0.5 g of the compound prepared in example 2 is introduced into 5 ml of a chloroform solution of 0.56 g of 2-phenylsulfonyl 2-phenyl oxaziridine, prepared as described in Org. Synth. 66 203–210 (1987). After being stirred for 1 hour at room temperature under an inert atmosphere, the mixture is concentrated under reduced pressure and the residue is chromatographed on a column of silica by eluting successively with a mixture of methylene chloride/methanol (95/5, then 90/10 v/v) and methylene chloride/methanol/25% (wt/v) aqueous NH$_4$OH (80/15/5 v/v).

0.35 g of the N-oxide, crystallized with 2 molecules of water, is thus obtained and melts at 115° C.

NMR$^1$H (DMSOd6) base: δ=8.56(d, 1H); 8.55(m, 1H); 7.73(m, 1H); 7.35(m, 1H); 7.01(s, 2H); 6.59(s, 1H); 4.79(s, 2H); 3.97(m, 2H); 3.47(m, 2H); 3.05(s, 6H); 2.87(m, 1H); 2.7(m, 2H); 1.21(d, 6H); 1.07(d, 12H).

EXAMPLE 90

2-(N-[2-N',N'-dimethylaminoethyl]N-[3-pyridylmethyl]amino) 5-bromo 4-(2,4,6-triisopropylphenyl) thiazole
(formula I: A=S; B=C; $Ar_1=2,4,6-[CH(CH_3)_2]_3-C_6H_2$; $R_3$=Br; $Ar_2$=3-pyridyl; $Z_1=(CH_2)_2$; $Z_2=CH_2$; $W=N(CH_3)_2$).

2.3 g of the compound prepared in example 2 are dissolved in 100 ml of a 0.05 N aqueous solution of hydrobromic acid, 0.8 g of bromine are introduced slowly and the mixture is heated at reflux for 30 minutes before being concentrated to dryness under reduced pressure. The residue, dissolved in a mixture of methylene chloride/methanol (95/5 v/v), is filtered through silica, then concentrated.

The residual solid is precipitated from ethanol by the addition of ethyl ether.

1.2 g of the dihydrobromide monohydrate of the desired compound are thus obtained which sublimes at about 250° C.

NMR$^1$H (DMSOd6) salt: δ=8.84(m, 2H); 8.30(m, 1H); 7.94(m, 1H); 7.05(s, 2H); 4.91(s, 2H); 3.94(t, 2H); 3.47(t, 2H); 2.86(s, 6H); 2.52(m, 3H); 1.24(d, 6H); 1.13(d, 6H); 1.01(d, 6H).

EXAMPLE 91

2-(N-[2-N',N'-dimethylaminoethyl]N-[3-pyridylmethyl]amino) 5-chloro 4-2,4,6-triisopropylphenyl) thiazole.
(Formula I: A=S; B=C; $Ar_1=2,4,6-[CH(CH_3)_2]_3-C_6H_2$; $R_3$=Cl; $Ar_2$=3-pyridyl; $Z_1=(CH_2)_2$; $Z_2=CH_2$; $W=N(CH_3)_2$).

2.3 g of the compound of example 2 are dissolved in a mixture of 80 ml of water and 10 ml of a 1N aqueous solution of HCl and 0.36 g of chlorine gas is introduced into the solution. After being left overnight at room temperature, the mixture is concentrated to dryness and about 20 ml of an ice-cold 2N aqueous solution of NaOH are added to the residue to give a distinctly basic pH. The aqueous phase is extracted with methylene chloride; after being washed and dried, the organic phase is concentrated and the residue is purified by chromatography on silica by eluting with a mixture of methylene chloride and methanol (98/2 v/v).

The dioxalate, prepared in acetone, melts at 178° C.

NMR$^1$H (DMSOd6) salt: δ=8.54(m, 2H); 7.70(m, 1H); 7.40(m, 1H); 7.06(s, 2H); 4.71(s, 2H); 3.82(t, 2H); 3.30(t, 2H); 2.76(s, 6H); 2.61(m, 3H); 1.24(d, 6H); 1.13(d, 6H); 1.04(d, 6H).

EXAMPLE 92

2-(N-[2-N',N'-dimethylaminoethyl]N-[3-pyridylmethyl]amino) 4-(4-carboxy 2,6-dimethylphenyl)thiazole
(Formula I: A=S; B=C; $Ar_1=4-(COOH)$ $2,6-(CH_3)_2-C_6H_2$; $R_3$=H; $Ar_2$=3-pyridyl; $Z_1=(CH_2)_2$; $Z_2=CH_2$; $W=N(CH_3)_2$).

A solution of 1.6 g of the compound of example 61 in 50 ml methanol is heated at reflux for 3 hours with a solution of 2.13 g of KOH in 50 ml of water; the mixture is neutralized at about 15° C. by addition of a 2N aqueous solution of HCl and the methanol is evaporated under reduced pressure. The aqueous phase is extracted with methylene chloride to give 1.4 g of the desired compound, crystallized with 0.5 H$_2$O and which melts at 125° C.

NMR$^1$H (DMSOd6-D$_2$O) base: δ=8.53(m, 2H); 7.72(m, 1H); 7.60(s, 2H); 7.35(m, 1H); 6.60(s, 1H); 4.72(s, 2H); 3.55(t, 2H); 2.47(t, 2H); 2.15(s, 6H); 2.10(s, 6H).

EXAMPLE 93

N-methyl N-2-([N'-[3-pyridylmethyl]N'-[4-(2,4,6-triisopropylphenyl)thiazole-2-yl]aminoethyl] acetamide
(Formula I: A=S; B=C; $Ar_1=2,4,6-[CH(CH_3)_2]_3-C_6H_2$; $R_3$=H; $Ar_2$=3-pyridyl; $Z_1=(CH_2)_2$; $Z_2=CH_2$; $W=NCH_3COCH_3$.

0.06 g of acetyl chloride is introduced into a solution containing 0.35 g of the compound of example 66 and 0.2 ml of triethylamine in 20 ml of dichloromethane at about 10° C. After 1 hour at room temperature, 20 ml of water are added and the organic phase is separated, from which 0.32 g of the expected compound is extracted in the form of an oil. The diphosphate, prepared in isopropanol and crystallized with 1.5 $H_2O$, melts at 165° C.

NMR$^1$H (DMSOd6) base: δ=8.5(m, 2H); 7.7(m, 1H); 7.4(m, 1H); 7(s, 2H); 6.55(m, 1H); 4.73(s, 2H); 3.55(m, 4H); 3–2.65(m, 6H); 1.90(s, 3H); 1.22(d, 6H); 1.05(d, 12H).

EXAMPLE 94

N-methyl N-2-([N'-[3-pyridylmethyl]N'[4-(2,4,6-triisopropylphenyl thiazole-2-yl]aminoethyl] methane sulfonamide (formula I: A=S; B=C; $Ar_1$=2,4,6-/$CH(CH_3)_2/_3$—$C_6H_2$; $R_3$=H; $Ar_2$=3-pyridyl; $Z_1$=$(CH_2)_2$; $Z_2$=$CH_2$; W=$NCH_3SO_2CH_3$).

Prepared by applying the process used in example 93 with methanesulfonyl chloride instead of acetyl chloride.

This compound, crystallized with ⅓ molecule of water, melts at 120° C.

NMR$^1$H (DMSOd6) base: δ=8.55(m, 2H); 7.72(m, 1H); 7.30(m, 1H); 7.02(s, 2H); 6.28(s, 1H); 4.78(s, 2H); 3.69(t, 2H); 3.40(t, 2H); 2.86(s, 3H); 2.80(m, 3H); 2.76(s, 3H); 1.26(d, 6H); 1.14(d, 12H).

EXAMPLE 95

N-methyl N'-methyl N'-2-([N''-[3-pyridylmethyl]N'' [4-(2,4,6-triisopropylphenyl)thiazole-2-yl] aminoethyl]thiourea (formula I: A=S; B=C; $Ar_1$=2,4,6-[$CH(CH_3)_2$]$_3$—$C_6H_2$; $R_3$=H; $Ar_2$=3-pyridyl; $Z_1$=$(CH_2)_2$; $Z_2$=$CH_2$; W=$NCH_3CSNHCH_3$).

0.08 g of methyl isothiocyanate are introduced into a solution of 0.5 g of the compound of example 66 in 5 ml of dichloromethane. After being stirred for 1 hour at room temperature, the mixture is evaporated to dryness and 10 ml of isopropyl ether are added to the residue. The precipitate is isolated and recrystallized from ethyl acetate to give 0.26 g of the desired compound which melts at 160° C.

NMR$^1$H (CDCl$_3$) base: δ=8.63(m, 2H); 7.90(s, 1H); 7.70 (m, 1H); 7.38(m, 1H); 7.04(s, 2H); 6.35(s, 1H); 4.61(s, 2H); 3.55(s, 4H); 3.26(s, 3H); 2.90(m, 1H); 2.70(m, 2H); 2.07(s, 3H); 1.22(d, 6H); 1.11(d, 12H).

EXAMPLE 96

N-methyl N'-methyl N'-2-([N''-[3-pyridylmethyl]N''-[4-(2,4,6-triisopropylphenyl)thiazole-2-yl]amino) ethyl]urea (formula I: A=S; B=C; $Ar_1$=2,4,6-[$CH(CH_3)_2$]$_3$—$C_6H_2$; $R_3$=H; $Ar_2$=3-pyridyl; $Z_1$=$(CH_2)_2$; $Z_2$=$CH_2$; W=$NCH_3CONHCH_3$).

This compound is prepared by applying the process used in example 95, by replacing methyl isothiocyanate by methyl isocyanate. It melts at 138° C.

NMR$^1$H (DMSOd6) base: δ=8.51(m, 2H); 7.69(m, 1H); 7.35(m, 1H); 7.02(s, 2H); 6.58(s, 1H); 6.48(d, 1H); 4.71(s, 2H); 3.55(m, 2H); 3.34(m, 2H); 2.72(m, 3H); 2.69(s, 3H); 2.15(d, 3H); 1.18(d, 6H); 1.05(d, 12H).

EXAMPLE 97

2-(N-[2-N',N'-dimethylaminoethyl]N-[3-pyridylmethyl]amino) 4-(4-amino 2,6-dimethylphenyl)thiazole (formula I: A=S; B=C; $Ar_1$=(4-$NH_2$-2,6-$(CH_3)_2$—$C_6H_2$; $R_3$=H; $Ar_2$=3-pyridyl; $Z_1$=$(CH_2)_2$; $Z_2$=$CH_2$; W=$N(CH_3)_2$).

A solution of 0.8 g of the compound of example 55 in a mixture of 5 ml of ethanol and 2 ml of a 12N aqueous solution of hydrochloric acid is heated at reflux for 4 hours. The solvents are then removed, the mixture is then made alkaline by addition of a 2N ice-cold aqueous solution of NaOH and extracted with ethyl acetate. The oil obtained by evaporation of the organic solvent is dissolved in acetone from which the trioxalate of the desired compound is precipitated by addition of a solution of 0.3 g of oxalic acid (dihydrate). 0.6 g of product, which melts at 157° C., is thus obtained.

NMR$^1$H (DMSOd6) salt: δ=8.55(m, 2H); 7.73(m, 1H); 7.41(m, 1H); 6.51(s, 1H); 6.29(s, 2H); 4.72(s, 2H); 3.86(t, 2H); 3.37(t, 2H); 2.81(s, 6H); 1.96(s, 6H).

TABLE 6

NMR $^1$H - 250 MHz

| Example No (amine or salt) | δ (ppm) |
|---|---|
| 3 | DMSOd6: 8.6(s, 1H); 8.55(m, 1H); 7.97(m, 1H); |
| salt | 7.68(m, 1H); 7.66(s, 1H); 7.55–7.36(m, 3H); 4.74(s, 2H); 3.98(m, 2H); 3.41(m, 2H); 2.84(s, 6H). |
| 4 | DMSOd6: 8.6(s, 1H); 8.52(m, 1H); 7.80(m, 1H); |
| salt | 7.53(m, 2H); 7.43(m, 2H); 6.92(s, 1H); 4.74(s, 2H); 3.90(t, 2H); 3.39(t, 2H); 2.62(s, 6H). |
| 5 | DMSOd6: 8.63(m, 2H); 7.8–7.4(m, 6H); 7.31(s, 1H); |
| salt | 4.69(s, 2H); 3.86(t, 2H); 3.34(t, 2H); 2.83(s, 6H). |
| 6 | DMSOd6: 8.5(m, 2H); 7.8(m, 3H); 7.3(m, 5H); 4.7(s, 2H); |
| salt | 4(t, 2H); 3.45(t, 2H); 2.9(s, 6H). |
| 7 | DMSOd6: 8.54(m, 2H); 7.82–7.58(m, 5H); 7.43(m, 1H); |
| salt | 6.94(s, 1H); 4.75(s, 2H); 3.93(t, 2H); 3.40(t, 2H); 2.82(s, 6H). |
| 8 | DMSOd6: 8.53(m, 2H); 7.75(m, 1H); 7.64(m, 2H); |
| salt | 7.41(m, 3H); 4.67(s, 2H); 3.91(t, 2H); 3.39(t, 2H); 2.84(s, 6H); 2.36(s, 3H). |
| 9 | DMSOd6: 8.59(m, 1H); 8.52(m, 1H); 7.74(m, 1H); |
| salt | 7.51(m, 2H); 7.42(m, 1H); 7.22(m, 2H); 4.67(s, 2H); 3.89(t, 2H); 3.39(t, 2H); 2.84(s, 6H); 2.35(s, 3H); 2.33(s, 3H). |
| 10 | DMSOd6: 8.6(m, 2H); 7.83(m, 1H); 7.38(m, 1H); |
| amine | 7.28(t, 1H); 6.67(d, 2H); 6.48(s, 1H); 4.70(s, 2H); 3.68(s, 6H); 3.48(t, 2H); 2.49(m, 2H); 2.16(s, 6H). |
| 11 | DMSOd6: 8.5(m, 2H); 7.25(m, 2H); 6.85(s, 2H); |
| salt | 6.6(s, 1H); 4.7(s, 2H); 3.9(t, 2H); 3.3(t, 2H); 2.7(s, 6H); 2.2(s, 3H); 2(s, 6H). |
| 12 | DMSOd6: 8.6(s, 1H); 8.47(m, 1H); 7.96(m, 1H); |
| amine | 7.75(m, 1H); 7.35(m, 1H); 7.25–7.1(m, 3H); 4.72(s, 2H); 3.55(m, 2H); 2.9–2.7(m, 4H); 2.48(m, 2H); 2.17(s, 6H); 1.95(m, 2H). |
| 13 | DMSOd6: 8.56(s, 1H); 8.51(m, 1H); 7.72(m, 1H); |
| salt | 7.40(m, 1H); 7.05(m, 3H); 4.67(s, 2H); 3.84(m, 2H); 3.32(m, 2H); 2.77(s, 6H); 2.28(s, 3H); 2.18(s, 3H); 2.08(s, 3H). |
| 14 | DMSOd6: 8.55(s, 1H); 8.47(m, 1H); 7.71(m, 1H); |
| amine | 7.33(m, 1H); 6.85(s, 2H); 6.48(s, 1H); 4.73(s, 2H); 3.54(m, 2H); 2.47(m, 2H); 2.22(s, 3H); 2.15(s, 6H); 2.03(s, 6H). |
| 15 | DMSOd6: 8.56(s, 1H); 8.48(m, 1H); 7.73(m, 1H); |
| salt | 7.35(m, 1H); 6.68(s, 1H); 6.63(s, 1H); 6.58(s, 2H); 6.51(s, 1H); 4.70(s, 2H); 3.66(s, 3H); 3.63(m, 2H); 2.73(m, 2H); 2.34(s, 6H); 2.27(s, 3H); 2.24(s, 3H). |
| 16 | DMSOd6: 8.63(s, 1H); 8.50(m, 1H); 7.80(m, 1H); |
| salt | 7.38(m, 1H); 6.57(s, 1H); 6.46(s, 1H); 6.26(s, 1H); 4.69(s, 2H); 3.80(s, 3H); 3.68(s, 6H); 3.63(m, 2H); 2.80(m, 2H); 2.40(s, 6H). |
| 17 | DMSOd6: 8.95(s, 1H); 8.90(m, 1H); 8.55(m, 1H); |
| salt | 8.05(m, 1H); 6.88(s, 2H); 6.77(s, 1H); 5.07(s, 2H); 3.75(t, 2H); 3.1(m, 2H); 2.72(s, 6H); 2.23(s, 3H); 2.15(m, 2H); 2.02(s, 6H). |
| 18 | DMSOd6: 8.9(m, 2H); 8.6(m, 1H); 8.1(m, 1H); 6.9(s, 2H); |
| salt | 6.7(s, 1H); 5.45(q, 1H); 3.9(t, 2H); 3.3(t, 2H); 2.8(s, 6H); 2.25(s, 3H); 2.0(s, 6H); 1.8(d, 3H). |

TABLE 6-continued

NMR $^1$H - 250 MHz

| Example No (amine or salt) | δ (ppm) |
|---|---|
| 19 salt | DMSOd6: 9(m, 2H); 8.1(m, 2H); 6.9(s, 2H); 6.8(s, 1H); 5.6(m, 1H); 4.1(t, 2H); 3.5(m, 2H); 2.9(s, 6H); 2.3(s, 3H); 2(s, 6H); 1.9(d, 3H). |
| 20 salt | DMSOd6: 8.57(s, 1H); 8.44(m, 1H); 7.75(m, 1H); 7.33(m, 1H); 6.84(s, 2H); 6.61(s, 4H); 6.49(s, 1H); 4.63(s, 2H); 4.36(q, 2H); 2.83(m, 1H); 2.47(m, 1H); 2.29(s, 6H); 2.22(s, 3H); 1.99(s, 6H); 1.20(d, 3H). |
| 21 salt | DMSOd6: 9.03(s, 1H); 8.90(m, 1H); 8.81(m, 1H); 8.63(m, 1H); 8.42(m, 1H); 8.10(m, 1H); 7.85(m, 2H); 6.84(s, 2H); 6.77(s, 1H); 5.29(s, 2H); 5.12(s, 2H); 2.20(s, 3H); 1.91(s, 6H). |
| 22 salt | DMSOd6: 9(m, 4H); 8.6(m, 2H); 8.3(m, 2H); 6.9(s, 2H); 6.8(s, 1H); 5.2(s, 4H); 2.3(s, 3H); 2.06(s, 6H). |
| 23 salt | DMSOd6: 9.30(s, 1H); 8.67(m, 2H); 8.47(m, 1H); 8.04(m, 1H); 7.87(s, 1H); 7.70(s, 1H); 6.85(s, 2H); 6.71(s, 1H); 5.01(s, 2H); 4.35(t, 2H); 3.61(t, 2H); 2.28(s, 2H); 2.24(s, 3H); 1.99(s, 6H). |
| 24 salt | DMSOd6: 8.55(s, 1H); 8.46(m, 1H); 7.72(m, 1H); 7.35(m, 1H); 6.65(s, 2H); 6.63(s, 3H); 6.5(s, 1H); 4.73(s, 2H); 3.62(m, 2H); 3.51(m, 4H); 2.59(m, 2H); 2.43(m, 4H); 2.22(s, 6H); 2.02(s, 6H). |
| 25 salt | DMSOd6: 8.55(s, 1H); 8.46(m, 1H); 7.72(m, 1H); 7.37(m, 1H); 6.6(s, 2H); 6.37(s, 1H); 4.7(s, 2H); 3.6(m, 2H); 2.65(m, 2H); 2.3(s, 6H); 2.2(s, 3H); 2.15(s, 6H); 1.92(s, 6H). |
| 26 amine | DMSOd6: 8.54(m, 2H); 7.7(m, 1H); 7.45(m, 1H); 6.85(s, 2H); 6.49(s, 1H); 4.74(s, 2H); 3.49(t, 2H); 2.6(m, 2H); 2.43(q, 4H); 2.22(s, 3H); 2.02(s, 6H); 0.9(t, 6H). |
| 27 salt | DMSOd6: 9(s, 1H); 8.88(m, 1H); 8.67(m, 1H); 8.09(m, 1H); 6.88(s, 2H); 6.78(s, 1H); 5.55(q, 1H); 3.64(t, 2H); 3.09(t, 2H); 2.70(s, 6H); 2.23(s, 3H); 2.10(m, 2H); 2.02(s, 6H); 1.83(d, 3H). |
| 28 amine | DMSOd6: 8.52(s, 1H); 8.48(m, 1H); 7.70(m, 1H); 7.58(s, 1H); 7.36(m, 1H); 7.11(s, 1H); 6.87(s, 3H); 6.52(s, 1H); 5.40(q, 1H); 3.98(t, 2H); 3.31(t, 2H); 2.23(s, 6H); 2.02(s, 6H); 1.95(m, 2H); 1.62(d, 3H). |
| 29 salt | DMSOd6: 8.53(m, 1H); 8.48(m, 1H); 7.70(m, 1H); 7.36(m, 1H); 6.85(s, 2H); 6.61(s, 3H); 6.50(s, 1H); 4.72(s, 2H); 3.55(m, 4H); 3.50(t, 2H); 2.37(m, 6H); 2.22(s, 3H); 2.02(s, 6H); 1.79(m, 2H). |
| 30 salt | DMSOd6: 8.9(m, 2H); 8.64(m, 1H); 8.09(m, 1H); 6.86(s, 2H); 6.73(s, 1H); 5.46(q, 1H); 3.99(t, 2H); 3.35(m, 4H); 3.12(m, 2H); 2.21(s, 3H); 2(s, 6H); 1.83(d, 3H). |
| 31 salt | DMSOd6: 9.00(s, 1H); 8.89(d, 1H); 8.62(d, 1H); 8.1(m, 1H); 7.5–7.3(m, 5H); 4.98(s, 2H); 4(t, 2H); 3.43(m, 2H); 2.81(s, 6H); 2.74(t, 2H); 1.51(m, 2H); 1.25(m, 6H); 0.82(t, 3H). |
| 32 amine | CDCl3: 8.70(m, 2H); 8.55(m, 2H); 7.8(m, 2H); 7.30(m, 2H); 6.9(m, 2H); 6.25(s, 1H); 5.35(q, 2H); 2.35(s, 3H); 2.1(s, 6H); 1.6(d, 6H). |
| 33 salt | DMSOd6: 8.55(s, 1H); 8.5(m, 1H); 7.8(m, 1H); 7.35(m, 1H); 6.85(s, 2H); 6.61(s, 4H); 6.5(s, 1H); 5.31(m, 1H); 3.5(m, 6H); 2.52(m, 1H); 2.4(m, 5H); 2.21(s, 3H); 2.05(s, 6H); 1.65(m, 3H). |
| 34 salt | DMSOd6: 8.85(m, 2H); 8.50(m, 1H); 8.01(m, 1H); 6.86(s, 2H); 6.72(s, 1H); 5.35(m, 1H); 4.01(m, 2H); 3.88(m, 1H); 3.47(m, 2H); 3.04(m, 2H); 2.22(s, 3H); 2.15–1.7(m, 13H); 1.15(m, 3H). |
| 35 salt | DMSOd6: 8.9(m, 2H); 8.6(m, 1H); 8.07(m, 1H); 6.87(s, 2H); 6.72(s, 1H); 5.48(q, 1H); 4(m, 2H); 3.45(m, 2H); 3.28(m, 2H); 2.92(m, 2H); 2.23(s, 3H); 2.00(s, 6H); 1.81(d, 3H); 1.70(m, 6H). |
| 36 salt | DMSOd6: 8.96(s, 1H); 8.89(m, 1H); 8.57(m, 1H); 8.10(m, 1H); 6.87(s, 2H); 6.75(s, 1H); 5.09(s, 2H); 4.12(m, 2H); 3.61(m, 2H); 3.42(m, 2H); 2.22(s, 3H); 2.02(s, 6H); 1.33(m, 12H). |
| 37 salt | DMSOd6: 8.95(s, 1H); 8.89(m, 1H); 8.62(m, 1H); 8.10(m, 1H); 6.87(s, 2H); 6.72(s, 1H); 5.39(m, 1H); 4.04(m, 2H); 3.60(m, 2H); 3.30(m, 2H); 2.23(s, 3H); 2.02(s, 6H); 1.82(m, 3H); 1.33(m, 3H); 1.26(m, 9H). |
| 38 salt | DMSOd6: 8.64(s, 1H); 8.48(m, 1H); 7.8(m, 1H); 7.66(s, 2H); 7.35(m, 1H); 7.31(s, 1H); 7.17(s, 1H); 6.59(s, 2H); 4.73(s, 2H); 3.75(m, 2H); 2.75(m, 2H); 2.38(s, 6H); 1.3(s, 18H). |
| 39 amine | CDCl3: 8.62(m, 1H); 8.53(m, 1H); 7.75(m, 1H); 7.65(s, 2H); 7.25(m, 1H); 6.54(s, 1H); 5.24(s, 1H); 4.79(s, 2H); 3.58(t, 2H); 2.59(t, 2H); 2.28(s, 6H); 1.46(s, 18H). |
| 40 salt | DMSOd6: 9.00(s, 1H); 8.95(m, 1H); 8.64(m, 1H); 8.13(m, 1H); 6.87(s, 2H); 6.74(s, 1H); 5.35(m, 1H); 3.94(m, 2H); 3.32(m, 2H); 3.08(m, 4H); 2.22(s, 3H); 2.02(s, 6H); 1.81(m, 3H); 1.54(m, 4H); 1.21(m, 4H); 0.8(t, 6H). |
| 41 amine | DMSOd6: 8.56(s, 1H); 8.46(m, 1H); 7.74(m, 1H); 7.35(m, 1H); 6.99(s, 2H); 6.50(s, 1H); 5.40(m, 1H); 3.41(m, 2H); 2.88(m, 2H); 2.69(m, 2H); 2.5–2.3(m, 2H); 2.10(m, 5H); 1.65(d, 3H) 1.21(m, 6H); 1.05(m, 12H). |
| 42 amine | DMSOd6: 8.43(s, 2H); 7.64(m, 1H); 7.32(m, 1H); 7.02(s, 2H); 6.49(s, 1H); 3.64(t, 2H); 3.49(t, 2H); 2.99(m, 2H); 2.88(m, 1H); 2.73(m, 2H); 2.50(m, 2H); 2.22(s, 6H); 1.22(d, 6H); 1.09(d, 12H). |
| 43 salt | DMSOd6: 8.50(s, 2H); 7.70(m, 1H); 7.35(m, 1H); 7(s, 2H); 6.55(s, 1H); 4.75(s, 2H); 3.5(t, 2H); 3.05(t, 2H); 2.95(m, 3H); 2.75(s, 6H); 2.05(m, 2H); 1.2(d, 6H); 1.05(d, 12H). |
| 44 amine | DMSOd6: 8.55(s, 1H); 8.45(m, 1H); 7.73(m, 1H); 7.34(m, 1H); 7.00(s, 2H); 6.54(s, 1H); 4.72(s, 2H); 3.6(m, 2H); 3.35(m, 2H); 2.77(m, 1H); 2.7(m, 2H); 2.5(m, 4H); 1.65(m, 4H); 1.20(d, 6H); 1.06(d, 12H). |
| 45 salt | DMSOd6: 8.55(s, 2H); 7.71(m, 1H); 7.40(m, 1H); 7.01(s, 2H); 6.65(s, 1H); 4.74(s, 2H); 3.68(m, 2H); 3.30(m, 2H); 3.15(m, 4H); 2.87(m, 1H); 2.68(m, 2H); 1.65(m, 4H); 1.47(m, 2H); 1.20(d, 6H); 1.08(d, 12H). |
| 46 salt | DMSOd6: 8.44(m, 2H); 7.70(m, 1H); 7.30(m, 1H); 7.15(m, 2H); 7.01(s, 2H); 6.70(m, 2H); 6.45(s, 1H); 5.06(s, 2H); 2.91(s, 6H); 2.8(m, 3H); 1.20(d, 6H); 1.07(d, 12H). |
| 47 salt | DMSOd6: 8.55(s, 2H); 7.65(m, 1H); 7.26(m, 1H); 7.02(s, 2H); 6.25(s, 1H); 4.75(s, 2H); 3.39(t, 2H); 2.82(m, 3H); 2.33(t, 2H); 2.25(s, 6H); 1.70(m, 2H); 1.51(m, 2H); 1.24(d, 6H); 1.16(d, 12H). |
| 48 salt | DMSOd6: 8.52(s, 2H); 7.71(m, 1H); 7.40(m, 1H); 6.35(s, 1H); 4.85(s, 2H); 3.86(t, 2H); 3.34(t, 2H); 2.84(s, 6H); 1.92–1.37(m, 1H). |
| 49 salt | DMSOd6: 8.63(s, 1H); 8.5(m, 1H); 7.8(m, 1H); 7.4(m, 1H); 7.3(s, 1H); 7.1(s, 2H); 4.73(s, 2H); 4(m, 2H); 3.83(s, 6H); 3.68(s, 3H); 3.43(m, 2H); 2.89(s, 6H). |
| 50 salt | DMSOd6: 8.58(s, 1H); 8.5(m, 1H); 7.7(m, 2H); 7.5(m, 3H); 4.68(s, 2H); 3.8(t, 2H); 3.26(t, 2H); 2.73(s, 6H); 2.1(s, 3H). |
| 51 salt | DMSOd6: 8.5(m, 2H); 7.7(d, 1H); 7.4(m, 1H); 7(m, 3H); 4.7(s, 2H); 3.84(m, 2H); 3.35(m, 2H); 2.8(s, 6H); 2.5(s, 3H); 2.3(s, 3H); 1.1(d, 6H). |
| 52 oase | DMSOd6: 8.61(m, 1H); 8.48(m, 1H); 7.76(m, 3H); 7.36(m, 1H); 7.20(m, 2H); 7.07(s, 1H); 4.77(s, 2H); 3.60(t, 2H); 2.53(t, 2H); 2.15(s, 6H); 1.78(m, 6H). |
| 53 salt | DMSOd6: 8.35(m, 1H); 7.6(m, 1H); 7.42(m, 1H); 6.86(s, 2H); 5.62(s, 1H); 4.74(s, 2H); 3.9(m, 2H); 3.3(m, 2H); 2.73(s, 6H); 2.23(s, 3H); 2.01(s, 6H). |
| 54 salt | DMSOd6: 8.57(s, 2H); 7.73(m, 1H); 7.40(m, 1H); 6.99(s, 1H); 6.85(s, 1H); 4.73(s, 2H); 3.91(t, 2H); 3.31(t, 2H); 2.77(m, 6H); 2.50(s, 3H); 2.35(s, 3H). |
| 55 salt | DMSOd6: 8.55(s, 1H); 7.70(m, 1H); 7.35(m, 1H); 7.15(s, 2H); 6.60(s, 1H); 4.70(s, 2H); 3.87(t, 2H); 3.30(t, 2H); 2.75(s, 6H); 2.02(s, 6H); 2.01(s, 3H). |
| 56 salt | DMSOd6: 8.53(m, 2H); 7.72(m, 1H); 7.57(s, 2H); 7.40(m, 1H); 6.80(s, 1H); 4.75(s, 2H); 3.88(t, 2H); 3.30(t, 2H); 2.75(s, 6H); 2.13(s, 6H). |
| 57 salt | DMSOd6: 8.53(m, 2H); 7.74(m, 1H); 7.59(s, 2H); 7.44(m, 1H); 6.72(s, 1H); 4.75(s, 2H); 3.85(m, 2H); 3.8(m, 0, 5H); 3.37(m, 2H); 2.80(s, 6H); 2.13(s, 6H); 1.05(d, 3H). |

TABLE 6-continued

NMR $^1$H - 250 MHz

| Example No (amine or salt) | δ (ppm) |
|---|---|
| 58 salt | DMSOd6: 8.53(m, 2H); 7.72(m, 1H); 7.41(m, 1H); 7.12(m, 3H); 6.66(s, 1H); 4.74(s, 2H); 3.90(t, 2H); 3.36(t, 2H); 2.80(s, 6H); 2.09(s, 6H). |
| 59 salt | DMSOd6: 8.55(m, 2H); 7.72(m, 1H); 7.27(m, 6H); 6.40(s, 1H); 4.84(s, 2H); 3.83(m, 4H); 2.75(s, 2H); 2.57(s, 6H). |
| 60 salt | DMSOd6: 8.86(m, 2H); 8.50(m, 1H); 8.04(m, 1H); 7.20(s, 2H); 4.87(s, 2H); 3.95(m, 2H); 3.42(m, 2H); 3.25(m, 1H); 2.87(s, 6H); 1.36(s, 18H); 1.23(d, 6H). |
| 61 salt | DMSOd6: 8.55(m, 2H); 7.74(m, 1H); 7.68(s, 2H); 7.40(m, 1H); 6.76(s, 1H); 4.75(s, 2H); 3.86(m, 5H); 3.40(m, 2H); 2.80(s, 6H); 2.16(s, 6H). |
| 62 salt | DMSOd6: 8.63–7.12(m, 9H); 6.95(s, 1H); 4.75(s, 2H); 3.99(t, 2H); 3.82(s, 3H); 3.43(t, 2H); 2.87(d, 6H). |
| 63 salt | DMSOd6: 8.64–7.49(m, 11H); 7.44(s, 1H); 4.78(s, 2H); 4.05(t, 2H); 3.47(t, 2H); 2.91(s, 6H). |
| 69 salt | DMSOd6: 8.66(s, 1H); 8.63(m, 1H); 7.97(m, 1H); 7.63(m, 1H); 6.67(s, 2H); 6.65(s, 1H); 4.8(s, 2H); 3.86(m, 2H); 3.59(m, 2H); 3.48(m, 2H); 3.07(m, 2H); 2.23(s, 3H); 2.03(s, 6H); 1.95(m, 2H); 1.81(m, 2H). |
| 70 salt | DMSOd6: 8.54(m, 1H); 8.47(m, 1H); 7.72(m, 1H); 7.38(m, 1H); 6.66(s, 2H); 6.53(s, 1H); 4.74(s, 2H); 3.61(t, 2H); 3.07(m, 4H); 2.68(m, 9H); 2.23(s, 3H); 2.02(s, 6H). |
| 71 amine | CDCl3: 8.90(m, 1H); 8.10(m, 2H); 7.65–7.8(m, 2H); 7.55(m, 1H); 6.89(s, 2H); 6.27(s, 1H); 4.99(s, 2H); 3.59(t, 2H); 2.61(t, 2H); 2.28(s, 3H); 2.26(s, 6H); 2.17(s, 6H). |
| 72 salt | DMSOd6: 7.9(m, 1H); 7.5(m, 1H); 7.4(m, 2H); 7.0(s, 2H); 6.55(s, 1H); 4.8(s, 2H); 4.1(t, 2H); 3.45(t, 2H); 2.66(s, 6H); 2.65(m, 3H); 1.20(d, 6H); 1.05(d, 12H). |
| 73 amine | DMSOd6: 7.56(d, 1H); 7.42(d, 1H); 7.38(s, 2H); 7.18(t, 1H); 7.01(t, 1H); 6.89(s, 2H); 6.47(s, 1H); 4.80(s, 2H); 3.77(s, 3H); 3.40(m, 2H); 2.43(m, 2H); 2.25(s, 3H); 2.13(s, 12H). |
| 74 salt | DMSOd6: 8.85(m, 2H); 8.45(m, 1H); 8.02(m, 1H); 7.01(s, 2H); 6.72(s, 1H); 4.99(s, 2H); 3.78(t, 2H); 2.87(m, 3H); 2.60(m, 4H); 1.15(m, 21H). |
| 75 salt | DMSOd6: 8.55(m, 2H); 7.70(m, 2H); 7.37(m, 2H); 6.85(s, 2H); 6.50(s, 1H); 4.67(s, 2H); 4.40(s, 2H); 3.7(m, 1H); 2.95(s, 3H); 2.83(s, 3H); 2.22(s, 3H); 2.01(s, 6H); 1.03(d, 6H). |
| 76 base | DMSOd6: 8.61(d, 1H); 8.50(m, 1H); 7.80(d, 1H); 7.38(m, 1H); 7.0(s, 2H); 6.58(s, 1H); 4.73(s, 2H); 4.36(s, 2H); 3.61(s, 3H); 2.85(m, 1H); 2.63(m, 2H); 1.20(d, 6H); 1.05(d, 12H). |
| 77 base | DMSOd6: 8.48(m, 2H); 7.65(m, 1H); 7.34(m, 1H); 7.0(s, 2H); 6.53(s, 1H); 4.75(s, 2H); 3.59(m, 4H); 3.23(s, 3H); 2.80(m, 3H); 1.20(d, 6H); 1.06(d, 12H). |
| 83 salt | DMSOd6: 8.55(m, 2H); 7.75(m, 1H); 7.43(m, 1H); 6.90(s, 2H); 4.78(s, 2H); 3.94(t, 2H); 3.35(t, 2H); 2.77(s, 6H); 2.26(s, 3H); 2.09(s, 3H); 2.03(s, 6H). |
| 84 salt | DMSOd6: 8.63(s, 1H); 8.54(m, 1H); 8.12(m, 2H); 7.80(m, 1H); 7.40(m, 4H); 4.78(s, 2H); 4.05(t, 2H); 3.42(t, 2H); 2.85(s, 6H). |
| 85 salt | DMSOd6: 8.8(m, 2H); 8.37(m, 1H); 7.97(m, 1H); 6.85(s, 2H); 4.96(s, 2H); 3.7(s, 3H); 3.6(m, 4H); 2.2(s, 3H); 2(s, 6H). |

We claim:

1. Compound of formula:

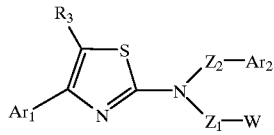

in which:

$Z_1$ is $C_1$–$C_4$ alkylene or phenylene;

when $Z_1$ is $C_1$–$C_4$ alkylene, W is $NR_1R_2$, in which $R_1$ is selected from H and $C_1$–$C_4$ alkyl, and $R_2$ is selected from H, $C_1$–$C_4$ alkyl, $CONQ_1Q_2$ and $CSNQ_1Q_2$ in which $Q_1$ and $Q_2$ are independently selected from H and $C_1$–$C_4$ alkyl, $SO_2Q_3$ in wich $Q_3$ is $C_1$–$C_4$ alkyl, $COOQ_4$ in which $Q_4$ is selected from $C_1$–$C_4$ alkyl and benzyl, or $R_1$ and $R_2$ taken together form with N a saturated heterocycle morpholine, pyrrolidine, piperidine, piperazine or 4-($C_1$–$C_3$)alkyl-piperazine; or W is $N(O)R_1R_2$ in which $R_1$, $R_2$ are independently selected from H and $C_1$–$C_4$ alkyl; or W is selected from the group consisting of $C_1$–$C_4$ alkoxy, and $C_1$–$C_4$ thioalkoxy;

when $Z_1$ phenylene, W is $NR_1R_2$ in which $R_1$ and $R_2$ are independently selected from H and $C_1$–$C_4$ alkyl;

$Z_2$ is $C_1$–$C_4$ alkylene;

$Ar_1$ and $R_3$ taken together form the group:

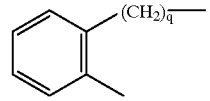

in which q is equal to 2 to 4; and $Ar_2$ is pyridyl, optionally substituted by a radical selected from $C_1$–$C_3$ alkyl, $C_1$–$C_3$ alkoxy and halogen; or a pharmaceutically acceptable acid or base salt thereof.

2. Compound according to claim 1 of formula I in which $Z_1$ $C_1$–$C_4$ alkylene and W is $NR_1R_2$.

3. A method for treating a disease associated with an excess of platelet-aggregating-factor-acether comprising administering to a patient in need thereof an effective amount of the compound of claim 1, in admixture with a pharmaceutically acceptable carrier.

4. Pharmaceutical composition comprising an effective amount of a compound according to claim 1, in which the salts are pharmaceutically acceptable, and at least one excipient.

* * * * *